United States Patent [19]

Hashimoto et al.

[11] Patent Number: 5,589,506
[45] Date of Patent: Dec. 31, 1996

[54] STILBENE DERIVATIVE AND STILBENE ANALOG DERIVATIVE, AND USE THEREOF

[75] Inventors: Koichi Hashimoto, Yokohama; Akio Yamada, Chigasaki; Hirokazu Hamano, Isehara; Shigehiro Mori, Zama; Hisako Moriuchi, Yokohama, all of Japan

[73] Assignee: Morinaga Milk Industry Co., Ltd., Tokyo, Japan

[21] Appl. No.: 331,618

[22] PCT Filed: Mar. 10, 1994

[86] PCT No.: PCT/JP94/00390

§ 371 Date: Dec. 30, 1994

§ 102(e) Date: Dec. 30, 1994

[87] PCT Pub. No.: WO94/20456

PCT Pub. Date: Sep. 15, 1994

[30] Foreign Application Priority Data

Mar. 10, 1993 [JP] Japan ................... 5-074992
Jun. 28, 1993 [JP] Japan ................... 5-182027
Aug. 5, 1993 [JP] Japan ................... 5-212097
Aug. 19, 1993 [JP] Japan ................... 5-225030

[51] Int. Cl.⁶ .................. A61K 31/275; C07C 255/34
[52] U.S. Cl. ............................. 514/520; 558/402
[58] Field of Search ................... 514/520, 720, 514/721, 525; 558/402; 568/646

[56] References Cited

U.S. PATENT DOCUMENTS

| | | | |
|---|---|---|---|
| 2,681,359 | 6/1954 | Rorig | 558/402 |
| 2,740,806 | 4/1956 | Rorig | 558/402 |
| 4,015,017 | 3/1977 | Gazave et al. | 558/402 |
| 4,326,055 | 4/1982 | Loeliger | 558/646 |
| 4,996,237 | 2/1991 | Pettit et al. | 514/720 |
| 5,091,569 | 2/1992 | Matsumoto et al. | 562/621 |
| 5,430,062 | 7/1995 | Cushman et al. | 514/520 |

FOREIGN PATENT DOCUMENTS 1046380 10/1966 United Kingdom .

OTHER PUBLICATIONS

Takatoshi et al, "Lipoxygenase inhibitors and their use as anti–allergy and anti–inflammatory agents", CA 122:29906, (1995).

Primary Examiner—José G. Dees
Assistant Examiner—Deborah Lambkin
Attorney, Agent, or Firm—Oblon, Spivak, McClelland, Maier & Neustadt, P.C.

[57] ABSTRACT

The present invention relates to a novel compound having a 12-lipoxygenase inhibitory effect, of the general formula (I), a precursor thereof, and a medicine containing the same,

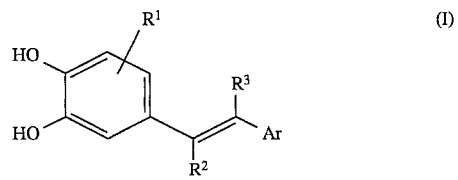

wherein $R^1$ represents a hydrogen atom or a hydroxy group; one of $R^2$ and $R^3$ represents a hydrogen atom, while the other cyano group ; and Ar is a group represented by the following general formula (a), (b) or (c),

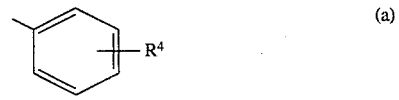

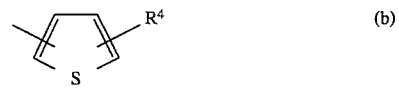

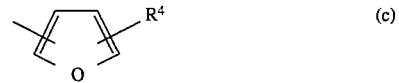

wherein $R^4$ represents a hydrogen atom, a lower alkyl group, a lower alkoxy group, a halogen atom, a thrifluoromethyl group or a cyano group.

15 Claims, No Drawings

STILBENE DERIVATIVE AND STILBENE ANALOG DERIVATIVE, AND USE THEREOF

This application is a 371 of PCT/JP44/00370.

TECHNICAL FIELD

The present invention relates to novel compounds of a stilbene derivative, a stilbene homologue derivative and an α,β-diarylacrylonitrile derivative inhibiting 12-lipoxygenase selectively, and medicines containing the above compounds as effective components; more specifically, the present invention relates to a stilbene derivative, a stilbene homologue derivative and an α,β-diarylacrylonitrile derivative having an effect of inhibiting the activities of 12-lipoxygenase on the 12-lipoxygenase route selectively, and medicines containing said compounds as effective components and inhibiting 12-lipoxgenase selectively useful as medicine for the prevention and remedies of various circulatory diseases such as arteriosclerosis and vasospasm and the prevention of the metastasis of some cancers (e.g., Lewis lung cancer).

In addition, the present invention relates to novel compounds of a stilbene derivative and a stilbene homologue derivative capable of forming a substance whose modified part is cleaved in vivo and which inhibits 12-lipoxygenase selectively, and medicines containing the above compounds as effective components; more specifically, the present invention relates to a stilbene derivative and a stilbene homologue derivative (hereinafter may be described as precursors) capable of being converted to compounds whose modified parts are cleaved in vivo and which inhibit 12-lipoxgenase on the 12-lipoxgenase route selectively, and medicines containing said precursors as effective components and inhibiting 12-lipoxgenase selectively useful as medicine for the prevention and remedies of various circulatory diseases such as arteriosclerosis and vasospasm and the prevention of the metastasis of some cancers.

The indication of percentage in the present specification means values by weight unless otherwise noted.

TECHNICAL BACKGROUND

It is known that a metabolic route called the 5-lipoxygenase route exists in arachidonate cascade and that arachidonate is converted to 5-hydroperoxyeicosatetraenoic acid (hereinafter may be described as 5-HPETE) by the function of 5-lipoxygenase ("Prostaglandin and Morbid States", edited by Seiitsu Murota, Tokyo Kagaku Dojin, 1984).

It is known that various leukotrienes are biosynthesized with this compound as an intermediate ("Prostaglandin and Morbid States", edited by Seiitsu Murota, Tokyo Kagaku Dojin, 1984), and it is also known that, for example, leukotriene B4 of these leukotrienes has a strong leukocyte migration effect and is a mediator of inflammations and that leukotriene C4 and D4 are mediators of asthma ("Prostaglandin and Morbid States", edited by Seiitsu Murota, Tokyo Kagaku Dojin, 1984).

Hence, searches for medicines having an inhibitory effect to 5-lipoxgenase have been performed broadly, from the viewpoint that if there is a medicine capable of inhibiting 5-lipoxgenase, an incipient enzyme of the biosynthesis system of these leukotrienes, effectively, the prevention and remedy effects of various diseases caused by the excess occurrence of leukotrienes (e.g., allergic diseases, bronchial asthma, dropsical swellings, various inflammatory diseases) may be anticipated.

On the other hand, a metabolic route called the 12-lipoxygenase route exists in arachidonate cascade. 12-lipoxygenase is an enzyme existing mainly in platelets and forms 12-hydroperoxyeicosatetraenoic acid (hereinafter may be described as 12-HPETE) according to a reaction with arachidonate, and the compound becomes 12-hydroxyeicosatetraenoic acid (hereinafter may be described as 12-HETE) according to reduction.

The physiological meaning of metabolic products on the 12-lipoygenase route has not been clear compared with that of the 5-lipoxgenase route; however, various physiological activities of the metabolic products have been made clear recently with 12-HPETE and 12-HETE of the main metabolic products at the center.

These physiological activities can be exemplified as below. Namely, regarding the metabolic product of 12-lipoxgenase, a possibility is pointed out that it may play a part in arteriosclerosis by accelerating functional control such as the aggregation and adhesion of platelets and the migration of vascular smooth muscle cells ("Gendai Iryo", Vol. 21, No. 11, pp. 3109–3113, 1989); a possibility is suggested that 12-HPETE may be an initiator for the occurrence of vasospasm after subarachnoid hemorrhage ("Gendai Iryo", Vol. 21, No. 11, pp. 3127–3130, 1989); in addition, it is shown that 12-HETE accelerates the adhesion and metastasis of some cancerous cells to vascular endothelial cells ("Gendai Iryo", Vol 22, special issue pp. 56–57, 1990)

According to the above facts, it is anticipated that substances inhibiting 12-lipoxgenase can be used effectively as medicine for the prevention and remedies of various circulatory diseases such as arteriosclerosis and vasospasm and the prevention of the metastasis of some cancers.

As a substance having an inhibitory effect to 12-lipoxygenase is known baicalein, a kind of natural flavonoid ("Biochemical and Biophysical Research Communications", Vol. 105, No. 3, pp. 1090–1095 1982).

In addition, a hydroxamic acid derivative (official gazette of Japanese Patent Kokai Publication No. 216961/1989, official gazette of Japanese Patent Kokai Publication No. 75 2/1990, official gazette of Japanese Patent Kokai Publication No, 196767/1990) and a caffeic acid derivative (official gazette of Japanese Patent Kokai Publication No. 275552/ 1989, official gazette of Japanese Patent Kokai Publication No. 235852/1990) are known.

On the other hand, a stilbene derivative and an α,β-diarylacrylonitrile derivative are generally synthesized chemically or separated from the natural world and purified; as compounds similar to the compounds of the present invention are known the following 1) to 6):

1) α-[(3,4-dihydroxyphenyl)methylene]-4-nitrobenzene acetonitrile "Journal of the Society of Dyers and Colourists", Vol. 92, No. 1, p. 14, 1976)
2) α-[(3,4-dihydroxy-5-nitrophenyl)methylene]-2-pyrimidine acetonitrile ["Journal of Computer-Aided Molecular Design", Vol. 6, No. 3, p. 253, 1992)
3) α-[(3,4-dihydroxyphenyl)methylene]-3,4-dihydroxybenzene acetonitrile (specification of U.S. Pat. No. 4,015, 017)
4) 2-(p-azidophenyl)-3-(3,4-dihydroxyphenyl)acrylonitrile (specification of French Invention Patent No. 1,513,907)
5) α'-cyano-3',4'-dihydroxy-4-stilbene carboxylic acid (specification of U.S. Pat. No. 2,766,271)
6) α'-(diphenylmethylene)-3,4-dihydroxy-benzene acetonitrile (specification of West Germany Patent Publication No. 2,501,443)

However, it has not been known at all that these compounds have 12-lipoxgenase inhibitory activities.

Incidentally, 12-lipoxgenase is an enzyme of relationship of 5-lipoxgenase; and a substance inhibiting either of enzymes may inhibit the other. In fact, a substance which reportedly has 5-lipoxgenase inhibitory activities and shows inhibitory activities also to 12-lipoxgenase is known, and most of hydroxamic acid derivatives are examples thereof.

Regarding the selectivity of inhibitory activities, such substances as can inhibit 12-lipoxgenase strongly and selectively are preferable for the prevention and remedies of diseases such as the above-mentioned circulatory diseases and the metastasis of cancer deemed to be caused mainly by 12-lipoxgenase metabolic products, though it depends upon the object of use.

DISCLOSURE OF THE INVENTION

According to such a situation, the present inventors have noted that baicalein, a kind of natural flavonoid, has relatively high 12-lipoxgenase inhibitory activities and a relatively high selectivity and succeeded in producing compounds having strong and highly selective 12-lipoxgenase inhibitory activities by employing the compound as a lead compound and performing the modification of its partial structure, which has led to the accomplishment of the present invention.

Moreover, generally, when one compound is utilized as a medicine, for example, an oral medicine, it is one of important requisites that the compound is absorbed into the body efficiently. As important factors having influence upon the efficient absorption are mentioned properties such as hydrophobicity and polarity of the compound.

The degrees of hydrophobicity and polarity of the above compound vary greatly as guessed from the variety of substituents. Hence, when the compound is used, for example, as an oral medicine, it does not always have hydrophobicity and polarity suitable for absorption from the intestinal tract.

Hence, regarding various modified compounds of these compounds, the present inventors have examined so-called prodrugs which can be absorbed in vivo efficiently by imparting them hydrophobicity or polarity suitable for medicine and can form primary compounds by being cleaved the modified part of the compounds rapidly or slowly according to objects by the function of enzyme present in vivo after absorption and as a result have found that a monoacyl material and a diacyl material of a catechol hydroxyl group possessed by these compounds in common are a group of compounds suited for the above object, which has led to the accomplishment of the present invention.

An object of the present invention is to provide a compound capable of inhibiting 12-lipoxgenase with a strong and high selectivity.

Another object of the present invention is to provide novel compounds of a stilbene derivative and a stilbene homologue derivative having use as so-called prodrugs which can be absorbed in vivo efficiently and can form compounds inhibiting 12-lipoxgenase by cleaving the modified part in vivo.

Another object of the present invention is to provide medicines inhibiting 12-lipoxgenase selectively which are useful as medicine for the prevention and remedies of various circulatory diseases such as arteriosclerosis and vasospasm caused by 12-lipoxygenase metabolic products and the prevention of the metastasis of some cancers and have low toxicity and few side effects.

A first embodiment of the present invention dissolving the above problems is a stilbene derivative or a stilbene homologue derivative represented by the following general formula:

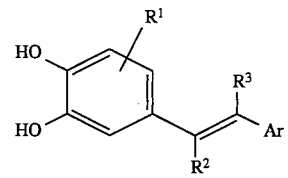

Formula 9

[wherein $R^1$ represents a hydrogen atom or a hydroxy group; $R^2$ and $R^3$ represent hydrogen atoms or cyano groups ($R^2$ and $R^3$ being different); and Ar is a group represented by the general formula 10, 11 or 12 below:

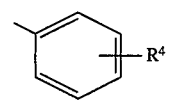

Formula 10

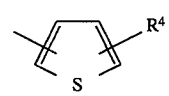

Formula 11

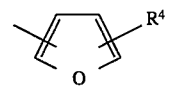

Formula 12 wherein $R^4$ represents a hydrogen atom, a lower alkyl group, a lower alkoxy group, a halogen atom, a trifluoromethyl group or a cyano group.]

A second embodiment of the present invention dissolving the above problems is a medicine containing a compound selected from a group consisting of a stilbene derivative and a stilbene homologue derivative or an admixture thereof represented by the following formula as an effective component:

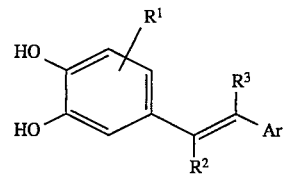

Formula 13

[wherein $R^1$ represents a hydrogen atom or a hydroxy group; $R^2$ and $R^1$ represent hydrogen atoms or cyano groups ($R^2$ and $R^3$ being different); and Ar is a group represented by the general formula 14, 15 or 16 below:

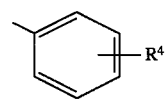

Formula 14

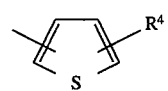

Formula 15

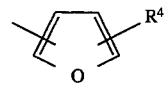

Formula 16 wherein $R^4$ represents a hydrogen atom, a lower alkyl group, a lower alkoxy group, a halogen atom, a trifluoromethyl group, a cyano group or a nitro group.]

The compound of the first embodiment of the present invention is stilbene or such stilbene homologue as one benzene ring of stilbene is replaced by a heterocycle ring represented by the general formula below:

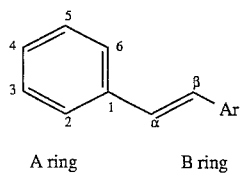

Formula 17

A ring   B ring and relates to a stilbene derivative or a stilbene homologue derivative characterized by having at least two catechol-type hydroxy groups in the A ring, having no hydroxy group in the B ring and having a cyano group bonded to either carbon of the double bond linking the A ring with the B ring.

A method of producing the compound relating to the first embodiment of the present invention can be exemplified as below.

A compound represented by the general formula below:

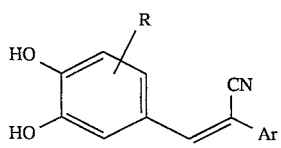

Formula 18

(wherein R is a hydrogen atom or a hydroxy group; and Ar is a group represented by the general formula 19, 20 or 21 below:

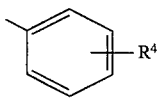

Formula 19

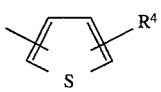

Formula 20

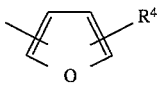

Formula 21 wherein $R^4$ represents a hydrogen atom, a lower alkyl group, a lower alkoxy group, a halogen atom, a trifluoromethyl group, a cyano group or a nitro group. Hereunder Ar will be described only as Ar.) can be synthesized according to the processes represented by the following formulae:

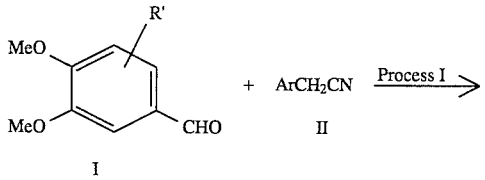

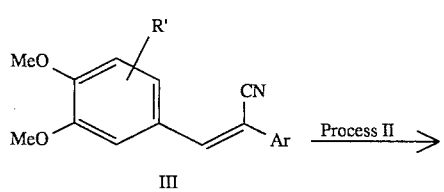

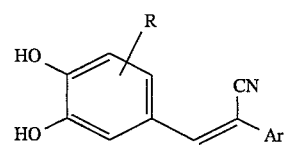

(wherein R represents a hydrogen atom or a hydroxy group; and R' represents a hydrogen atom or OMe.)

The compound (III) can be obtained by condensing a desired benzaldehyde derivative (I) and arylacetonitrile (II) under the reaction conditions known as Knoevenagel condensation (Process I). Subsequently, the desired compound can be obtained by reacting the above compound with a demethylated reagent such as boron tribromide, trimethylsilyl iodide or pyridinium chloride (Process II).

When arylacetonitrile (II) to be used in the condensation reaction has relatively rich reactivity, the desired compound can be obtained by subjecting the compound and hydroxybenzaldehyde (IV) to Knoevenagel condensation reaction according to the process represented by the following formulae (Process III):

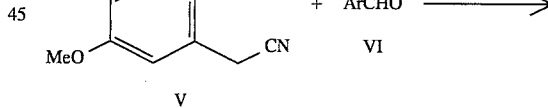

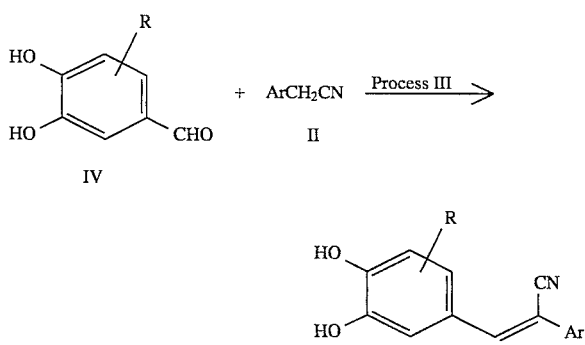

Besides, the compound represented by the general formula below:

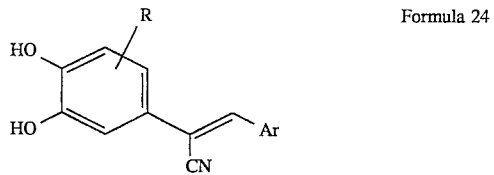

Formula 24

(wherein R is hydrogen or a hydroxy group) can be synthesized according to the processes represented by the following formulae:

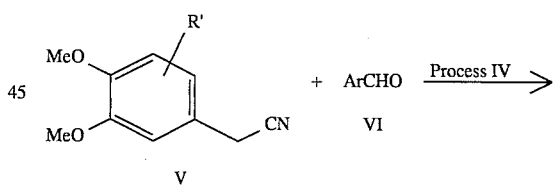

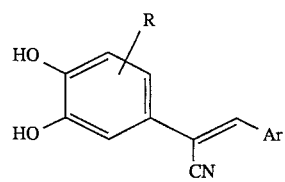

(wherein R represents a hydrogen atom or a hydroxy group; and R' represents a hydrogen atom or OMe.)

The compound (VII) can be obtained by condensing a desired phenylacetonitrile derivative (V) and aromatic aldehyde (VI) under the reaction conditions known as Knoevenagel condensation (process IV). Subsequently, the desired compound can be obtained by demethylating the compound in the same manner as in the above Process II (Process V).

The thus obtained compounds of the present invention can be purified according to a known purification method such as recrystallization or chromatography. Incidentally, though cis- and transgeometric isomers exist in the compounds of the present invention, all of them are included in the compounds of the present invention.

Since the above compounds of the present invention have a 12-lipoxgenase inhibitory effect selectively, they have effects of inhibiting the formation of 12-lipoxygenase metabolic products such as 12-HPETE and 12-HETE, and the medicines of the present invention containing said compounds as effective components and inhibiting 12-lipoxgenase selectively can be utilized as medicine for the prevention and remedies of various circulatory diseases such as arteriosclerosis and vasospasm and the prevention of the metastasis of some cancers effectively.

A third embodiment of the present invention is a stilbene derivative and a stilbene homologue derivative represented by the following general formula:

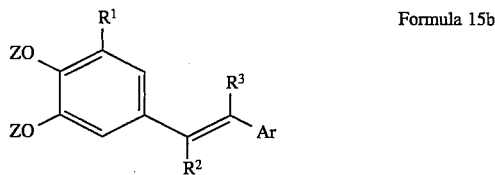

Formula 15b

[wherein $R^1$ represents a hydrogen atom or OZ ; $R^2$ and $R^3$ represent hydrogen atoms or cyano groups ($R^2$ and $R^3$ being different); and Ar is a group represented by the general formula 16b, 17b or 18b below:

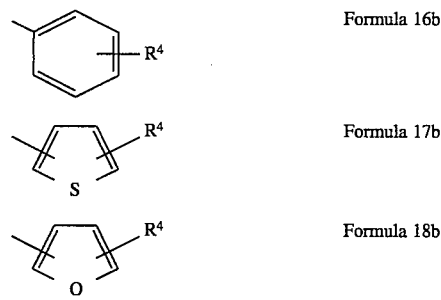

Formula 16b

Formula 17b

Formula 18b wherein $R^4$ represents a hydrogen atom, a lower alkyl group, a lower alkoxy group, a halogen atom, a trifluoromethyl group, a cyano group or a nitro group; Z is independently a hydrogen atom or a group represented by the general formula 19b (all Z not being hydrogen atoms):

Formula 19b wherein $R^5$ represents a straight-chain or branched-chain alkyl group or alkenyl group having carbon atoms of 1 to 20.]

A fourth embodiment of the present invention dissolving the above problems is a medicine containing a compound selected from a group consisting of a stilbene derivative and a stilbene homologue derivative or an admixture thereof represented by the following general formula as an effective component:

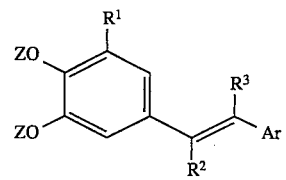

Formula 20b

[wherein $R^1$ represents a hydrogen atom or OZ ; $R^2$ and $R^2$ represent hydrogen atoms or cyano groups ($R^2$ and $R^3$ being different); and Ar is a group represented by the general formula 21b, 22b or 23b below:

Formula 21b

Formula 22b

Formula 23b wherein $R^4$ represents a hydrogen atom, a lower alkyl group, a lower alkoxy group, a halogen atom, a trifluoromethyl group, a cyano group or a nitro group; Z is independently a hydrogen atom or a group represented by the general formula 24b (all Z not being hydrogen atoms):

Formula 24b wherein $R^5$ represents a straight-chain or branched-chain alkyl group or alkenyl group having carbon atoms of 1 to 20.]

A method of producing the compound (precursor) of the third embodiment of the present invention can be exemplified as below. Namely, the compound of the present invention can be synthesized by the processes represented by the following formulae:

Process A

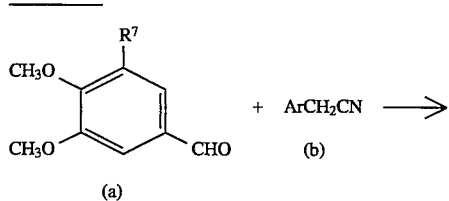

(a)  + ArCH$_2$CN  $\longrightarrow$   (b)

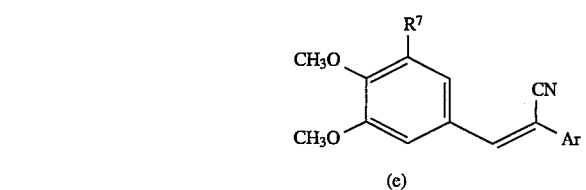

(e)

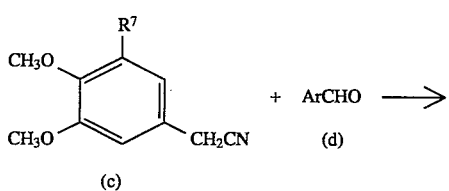

(c)  + ArCHO  $\longrightarrow$   (d)

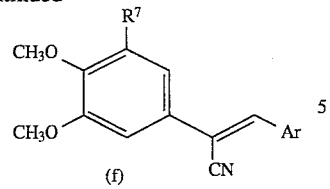

(f)

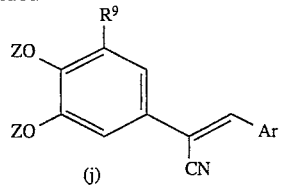

(j)

Process B

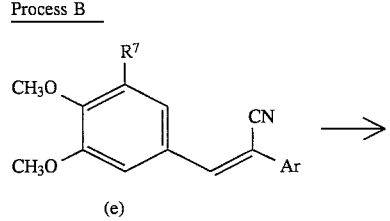

(e)

(g)

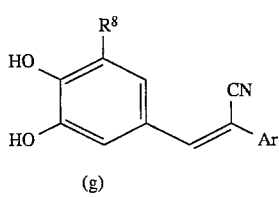

(f)

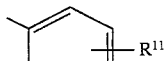

(h)

Process C

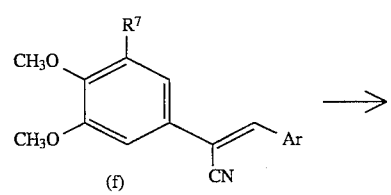

(g)

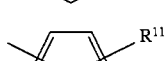

(i)

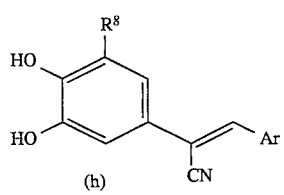

(h)

In the above formulae, $R^7$ represents a hydrogen atom or a methoxy group; $R^8$ represents a hydrogen atom or a hydroxy group; $R^9$ represents a hydrogen atom or OZ; Z is a group represented by the general formula 27b:

$$R^{10}-\overset{O}{\underset{\|}{C}}-$$  Formula 27b wherein $R^{10}$ represents a straight-chain or branched-chain alkyl group or alkenyl group having carbon atoms of 1 to 20; Ar is a group represented by the general formula 28b, 29b or 30b below:

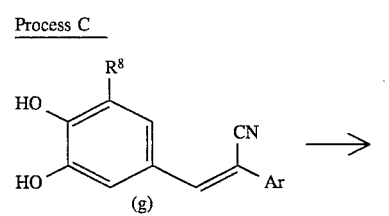 Formula 28b

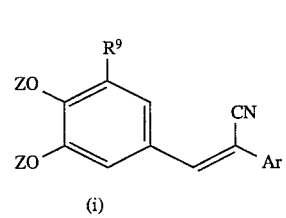 Formula 29b

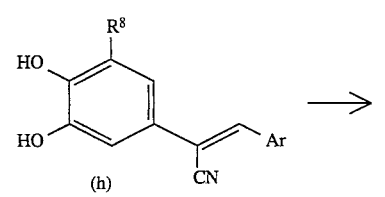 Formula 30b wherein $R^{11}$ represents a hydrogen atom, a lower alkyl group, a lower alkoxy group, a halogen atom, a trifluoromethyl group, a cyano group or a nitro group.

Namely, the compound (e) or (f) can be obtained by condensing 3,4-dimethoxybenzaldehyde or 3,4,5-trimethoxybenzaldehyde (a) and desired arylacetonitrile (b), or 3,4-dimethoxyphenylacetonitrile or 3,4,5-trimethoxyphenylacetonitrile (c) and desired aromatic aldehyde (d) under the reaction conditions known as Knoevenagel condensation (Process A).

Subsequently, the compound (g) or (h) can be obtained by reacting these compounds with a demethylating agent such as pyridinium chloride (Process B). Further, the compound (i) or (j) of the present invention can be obtained by reacting these compounds with a desired acylating agent such as acid chloride and acid anhydride in the presence of a base such as triethylamine or pyridine. In this case, partially acylated compounds can be obtained by regulating the equivalent relationship of an acylating agent (Process C).

When arylacetonitrile (b) in the Process A has relatively rich reactivity, the compounds can also be obtained according to the process represented by the following formulae:

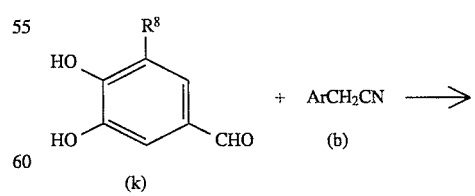

(k)  (b)

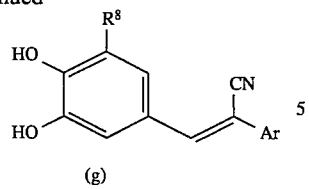

(g)

In the above formulae, $R^8$ represents a hydrogen atom or a hydroxy group.

Namely, the compound (g) can be obtained directly by subjecting 3,4-dihydroxybenzaldehyde or 3,4,5-trihydroxybenzaldehyde (k) instead of 3,4-dimethoxybenzaldehyde or 3,4,5-trimethoxybenzaldehyde and desired arylacetonitrile (b) to Knoevenagel condensation.

As an acyl group as a modified part of the compounds of the present invention can be used those with various carbon numbers, and various groups including monoacyl, diacyl and triacyl groups are used to produce compounds having desired hydrophobicity and polarity. An acyl group has no particular restriction so far as it is absorbed in vivo, cleaved and its forming free acid can be accepted medically and pharmaceutically; however, when an acyl group is cubically voluminous, the decrease of a hydrolysis rate due to esterase is observed, Hence, it is also possible by utilizing the above fact to control the cleavage of the compounds of the present invention in vivo by selecting the kind of an acyl group as a modified part.

The thus obtained compounds of the present invention can be purified according to a known purification method such as recrystallization or chromatography. The purified compounds of the present invention are remarkably stable and can exist free from any change for a long period of time even if they come into contact with an aqueous solution with a pH of 1 to 8. Incidentally, there exist cis- and trans-geometric isomers in the compounds of the present invention, all of which are included in the compounds of the present invention.

The above compounds of the present invention are absorbed in vivo, acyl groups are cleaved due to the function of enzymes present in vivo and compounds formed as a result have a strong 12-lipoxgenase inhibitory effect selectively, and hence have an effect of inhibiting the formation of 12-lipoxgenase metabolic products such as 12-HPETE and 12-HETE and can be utilized as medicine for the remedies and prevention of various circulatory diseases such as arteriosclerosis and vasospasm caused by these metabolic products and the prevention of the metastasis of some cancers effectively.

A fifth embodiment of the present invention dissolving the above problems is an α,β-diarylacrylonitrile derivative represented by the general formula 11c below:

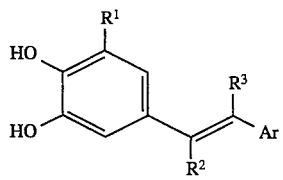

Formula 11c

[wherein $R^1$ represents a hydrogen atom or a hydroxy group; $R^2$ and $R^3$ represent hydrogen atoms or cyano groups ($R^2$ and $R^3$ being different); and Ar is a group represented by the general formula 12c or 13c below:

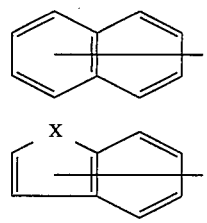

Formula 12c

Formula 13c wherein X represents an oxygen atom or a sulfur atom.]

A sixth embodiment of the present invention dissolving the above problems is a medicine containing a compound selected from a group consisting of α,β-diarylacrylonitrile derivatives represented by the general formula 14c below or an admixture thereof as an effective component:

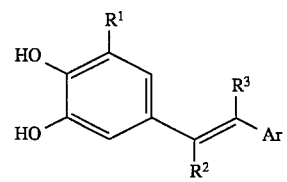

Formula 14c

[wherein $R^1$ represents a hydrogen atom or a hydroxy group; $R^2$ and $R^3$ represent hydrogen atoms or cyano groups ($R^2$ and $R^3$ being different); and Ar is a group represented by the general formula 15c or 16c below:

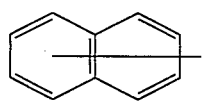

Formula 15c

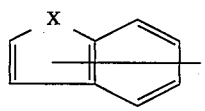

Formula 16c wherein X represents an oxygen atom or a sulfur atom.]

A method of producing the compound of the fifth embodiment of the present invention can be exemplified as below. Namely, the compound of the present invention can be synthesized according to the processes represented by the following formulae:

Process A

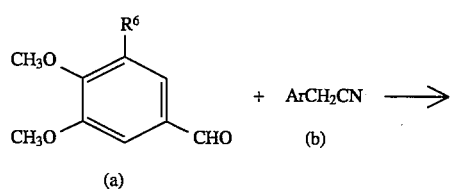

(a)

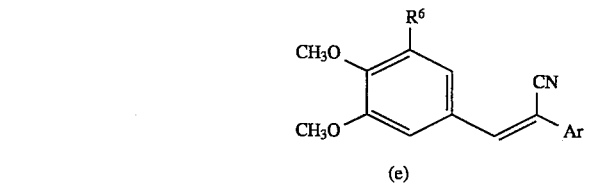

(e)

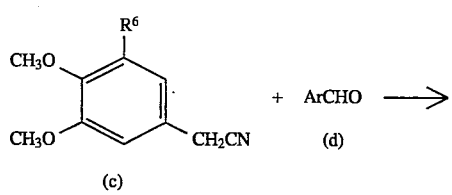

(c)

13
-continued

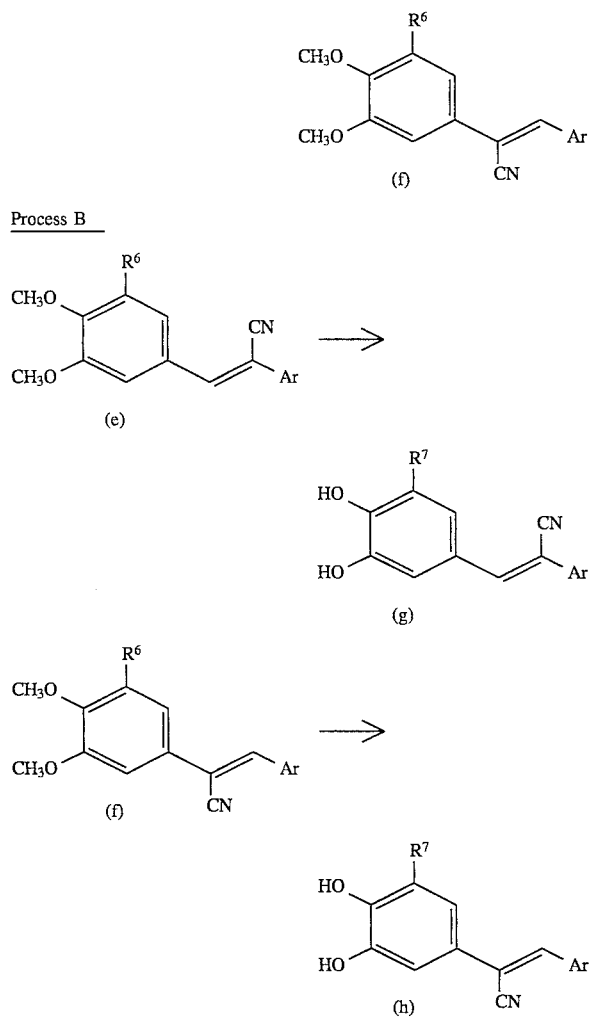

Process B (wherein, $R^6$ represents a hydrogen atom or a methoxy group; $R^7$ represents a hydrogen atom or a hydroxy group; Ar is a group represented by the general formula 18c or 19c below:

Formula 18c

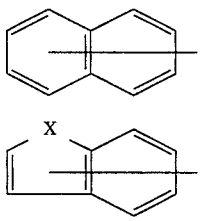

Formula 19c wherein X represents an oxygen atom or a sulfur atom.)

Namely, in the above formulae, the compound (e) or (f) can be obtained by condensing 3,4-dimethoxybenzaldehyde or 3,4,5-trimethoxybenzaldehyde (a) and desired arylacetonitrile (b), or 3,4-dimethoxyphenylacetonitrile or 3,4,5-trimethoxyphenylacetonitrile (c) and desired aromatic aldehyde (d) under the reaction conditions known as Knoevenagel condensation (Process A). Subsequently, the α,β-diarylacrylonitrile derivative compound (g) or (h) of the present invention can be obtained by reacting these compounds with a demethylating agent such as pyridinium chloride (Process B).

In this case, when arylacetonitrile (b) in the Process A has relatively rich reactivity, the compounds can also be obtained according to the process represented by the following formulae (Process C):

Process C

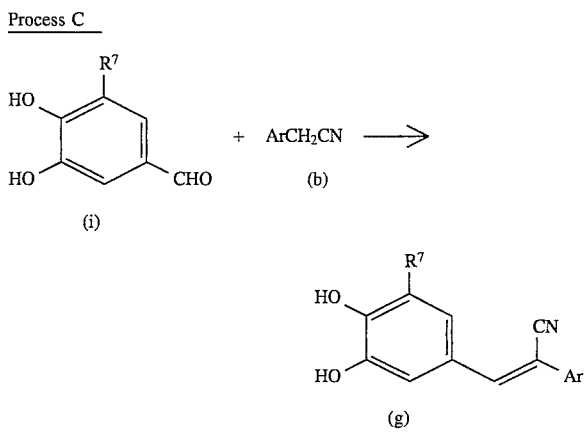

In the above formulae, $R^7$ represents a hydrogen atom or a hydroxy group.

Namely, the α,β-diarylacrylonitrile derivative compound (g) of the present invention can be obtained directly by subjecting 3,4-dihydroxybenzaldehyde or 3,4,5-trihydroxybenzaldehyde (i) instead of 3,4-dimethoxybenzaldehyde or 3,4,5-trimethoxybenzaldehyde (a) in Process A and desired arylacetonitrile (b) to Knoevenagel condensation.

The thus obtained compounds of the present invention can be purified according to a known purification method such as recrystallization or chromatography. Incidentally, there exist cis- and trans-geometric isomers in the compounds of the present invention, all of which are included in the compounds of the present invention.

The above compounds of the present invention have a 12-lipoxgenase inhibitory effect selectively and hence have an effect of inhibiting the formation of 12-lipoxygenase metabolic products such as 12-HPETE and 12-HETE, and medecines of the present invention containing said compounds as effective components and inhibiting 12-lipoxygenase selectively can be utilized as medicine for the remedies and prevention of various circulatory diseases such as arteriosclerosis and vasospasm caused by these metabolic products and the prevention of the metastasis of some cancers effectively.

The compounds of the present invention may be used as they are or as medicines in proper forms such as tablets, capsules, 23 jectable solutions, granules, depositories or the like by admixing them with a pharmaceutically acceptable known carrier or excipien or the like.

The medicines with the compounds of the present invention as effective components may be administered orally or parenterally according to injection, inhalation, coating or the like.

The administration dose may vary with patients to be cured, conditions of patients, ages, terms of treatment or the like and preferably may be administered usually in a dose range from about 0.1 mg to 50 mg once to three times per day.

Next, the present invention will be described in detail according to Test Examples.

Test Example 1

The test was performed to examine inhibitory effect of various compounds on the 12-lipoxyganase activity.
1) Preparation of Enzyme Solution A Sprague Dawley male rat was anesthetized with ether and bled from abdominal aorta using a syringe filled with about one-tenth volume of 3.8% sodium citrate. Blood was centrifuged at 180×g for 15 minutes at room temperature to pellet sanguineous platelet blood plasma. The resultant supernatant was again centrifuged at 1800×g for 10 minutes at 4° C. The pelleted platelets were rinsed twice with a washing buffer (50 mM Tris-hydrochloric acid buffer containing 154 mM sodium chloride and 2 mM EDTA, pH: 7.4). The platelets were then suspended in one-twentieth volume of a resuspension buffer (50 mM Tris-hydrochloric acid buffer containing 154 mM sodium chloride and 5.5 mM glucose, pH: 7.4). The platelets were then sonicated at 4° C. and centrifuged at 100,000×g for 30 minutes to obtain a supernatant as a 12-lipoxgenase enzyme solution.

2) Procedure for 12-lipoxgenase inhibition assay

The enzyme solution described above was diluted with the resuspension buffer above mentioned to prepare an assay solution so as to include about 2 mU/ml of 12-lipoxygenase. To an aliquot (300 µl) of the assay solution was added 1 µl of a 3 mM indomethacin-ethanol solution, 1 µl of an aqueous 300 mM reduced-glutathione solution, and 3 µl of varied concentrated test compounds solution in ethanol prepared in the same manner as Example 1 and Comparative Examples 1–9. The resultant mixture was incubated at 37° C. for 5 minutes. Subsequently, 3 µl of a 2.5 mM arachidonic acid solution in ethanol was added to incubate with for another 5 minutes at 37° C., then the reaction was ceased by the addition of 600 µl of methanol. After being centrifuged at 10,000×g for 5 minutes, 12-hydroxyeicosatetraenoic acid recovered in the supernatant was separated with a reverse phase high-performance liquid chromatography equipped with a C-18 of fiene at 234 nm to column and measured the absorption quantify the activity of 12 lipoxygenase. Values represent the concentration to produce 50% inhibition of 12 lipoxygenase activity were estimated from experimental data of each sample (hereinafter was described as the $IC_{50}$).

3) Results of the Test

The results of the test are as shown in Table 1 and Table 2. In Table 1 are shown the 12-lipoxgenase inhibition ratios of the compounds of Comparative Examples 1–4 whose $IC_{50}$ values could not be obtained and that of the compound of Example 1 according to the present invention for comparison; and in Table 2 are shown the compounds of Comparative Examples 5–9 whose $IC_{50}$ values could be obtained in contrast to the compound (Example 1) of the present invention.

As is apparent from Table 1 and Table 2, it was revealed that while the 12-lipoxgenase inhibitory effect of the compound of Example 1 according to the present invention is of an inhibition ratio of 97% at a concentration of $10^{-8}$M and an inhibition ratio of 73% at a concentration of $10^{-8}$M, the 12-lipoxygenase inhibitory effect of the compounds of Comparative Examples 1–4 was of an inhibition ratio of only less than 10% at a concentration of $10^{-5}$M though they are similar to the compound of the present invention in chemical structures.

The above results suggest that it is essential that the compound of the present invention has at least two cathecol-type hydroxy group in the A ring represented by the general formula below with a view to exhibiting a strong 12-lipoxygenase inhibitory effect:

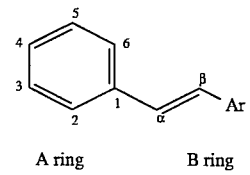

Formula 26

A ring      B ring

In addition, it was found that the 12-lipoxygenase $IC_{50}$ inhibitory effect of the compound having no cyano group in a double bond linking the A ring and the B ring (Comparative Example 5), the compound having an ethoxycarbonyl group instead of a cyano group (Comparative Example 6) and the compounds having a hydroxy group or a carboxy group in the B ring (Comparative Examples 7–9) is remarkably poor compared with that of the compound (Example 1) of the present invention. Incidentally, as a result of performing a test upon other compounds of the present invention, almost the same results were obtained.

TABLE 1

Results of the Test upon Inhibition Ratios

| Compound | 12-Lipoxygenase inhibition ratio (%) | | | | |
|---|---|---|---|---|---|
| | $10^{-5}$ | $10^{-6}$ | $10^{-7}$ | $10^{-8}$ | $10^{-9}$ |
| Ex. 1 | 97 | 97 | 98 | 73 | 1 |
| Comp. Ex. 1 | 7 | 1 | 0 | — | — |
| Comp. Ex. 2 | 10 | 2 | 5 | — | — |
| Comp. Ex. 3 | 10 | 1 | 0 | — | — |
| Comp. Ex. 4 | 2 | 0 | 0 | — | — |

Note:
1) Numerical values on line 3 show the mole concentrations of the compounds.
2) — shows that no measurement was performed.

TABLE 2

Results of the Test upon Inhibition Effect

| Compound | 12-Lipoxygenase $IC_{50}$ values |
|---|---|
| Ex. 1 | $4.2 \times 10^{-9}$ |
| Comp. Ex. 5 | $1.2 \times 10^{-6}$ |
| Comp. Ex. 6 | $1.6 \times 10^{-7}$ |
| Comp. Ex. 7 | $2.3 \times 10^{-7}$ |
| Comp. Ex. 8 | $3.0 \times 10^{-7}$ |
| Comp. Ex. 9 | $5.0 \times 10^{-6}$ |

Test Example 2

The test was carried out to examine the selectivity toward 12-lipoxgenase of the compounds of the first embodiment in the present invention.

1) Preparation of Enzyme Solution i) Preparation of 5-lipoxygenase enzyme solution Rat basophilic leukemia cells (RBL-1, ATCC CRL1378) were cultured in Dulbecco modified Eagle's medium containing 10% new-born bovine serum.

Cultured cells were collected and washed twice with a 50 mM Tris-buffered saline (containing 154 mM sodium chloride, pH: 7.4, hereinafter described as TBS). The cell suspension (4×107 cells/ml) was then sonicated and centrifuged at 10,000×g for 10 minutes.

The resultant supernatant was used to prepare an assay solution.

ii) Preparation of 12-lipoxgenase enzyme solution

The enzyme solution was prepared according to the same manner as in Test Example 1.

2) Method of Measurement of Enzymes Activity
i) Procedure for 5-lipoxgenase inhibition assay To an aliquot (15 μl) of the enzyme solution (40 mU/ml equivalent) was added 185 μl of TBS, 50 μl of a 2 mM adenosine triphosphate in TBS, 50 μl of a 12 mM calcium chloride in TBS, 1 μl of a 3 mM indomethacin in ethanol solution, 1 μl of an aqueous 300 mM reduced glutathione solution, and 3 μl of varied concentrated test compounds solution in ethanol. The resultant mixture was incubated at 37° C. for 5 minutes. Subsequently, 3 μl of a 2.5 mM arachidonic acid solution in ethanol was added to incubate the mixture for 2 minutes at 37° C. The reaction was ceased by the addition of 600 μl of methanol After being centrifuged at 10,000×g for 5 minutes, 5-hydroxyeicosatetraenoic acid recovered in the supernatant was separated with a reverse phase high-performance liquid chromatography equipped with a C-18 column and measured the absorption of diene at 234 nm to quantify the activity of the enzyme.

Using the compounds of the present invention prepared in the same manner as Examples 1–6, Example 9, Example 11, Examples 13–17, and Examples 20–27 as test samples and known baicalein (purchased from Wako Junyaku Kogyo) represented by the following formula as a control, the tests were performed for dose dependent inhibition to estimate $IC_{50}$ values:

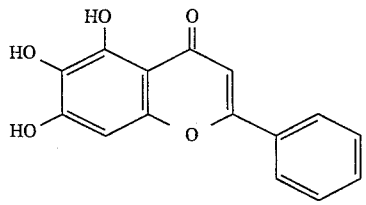

Formula 27 ii) Procedure for 12-lipoxgenase inhibition assay

The inhibition assay was performed according to the same method as described in Test Example 1 except that the same samples used in measurement of the 5-lipoxygensase activity were used to estimate $IC_{50}$ values.

3) Results of the Test

The results of the test are as shown in Table 3. As is apparent from Table 3, a remarkably strong inhibitory effect to 12-lipoxgenase was recognized in the compounds of the present invention, and $IC_{50}$ values were of the order of $10^{-9}$ mole/l, which were equivalent to that of known baicalein or more. On the other hand, the compounds of the present invention have an inhibitory effect also to 5-lipoxgenase; and the $IC_{50}$ values thereof were 10 to 30 times or more those to 12-lipoxgenase. Thus, it was revealed that the compounds of the present invention have an inhibitory effect to 12-lipoxgenase selectively.

Among the compounds of the present invention, those having a relatively large substituent in the B ring tend to exhibit a stronger 12-lipoxgenase inhibitory effect; when the B ring is a benzene ring, compounds with a substituent present in the p-position are preferable, and when it is a thiophene ring or a furan ring, those with a substituent present in the m-position to the substitution place of a double bond linking with the A ring are preferable.

As substituents, a chlorine atom or a bromine atom in case of a halogen atom, a methyl group or an ethyl group in case of an alkyl group and a methoxy group in case of an alkoxy group exhibited a 12-lipoxgenase inhibitory effect particularly remarkably.

Incidentally, as a result of performing a test upon other compounds of the present invention, almost the same results were obtained.

TABLE 3

Results of the Test upon the Selectivity of an Inhibition Effect

| Compound | $IC_{50}$ values of 12-lipoxygenase (mole) | $IC_{50}$ values of 5-lipoxygenase (mole) |
|---|---|---|
| Ex. 1 | $4.2 \times 10^{-9}$ | $3.8 \times 10^{-8}$ |
| Ex. 2 | $1.8 \times 10^{-9}$ | $5.6 \times 10^{-8}$ |
| Ex. 3 | $4.8 \times 10^{-9}$ | $9.4 \times 10^{-8}$ |
| Ex. 4 | $3.6 \times 10^{-9}$ | $1.5 \times 10^{-8}$ |
| Ex. 5 | $5.4 \times 10^{-9}$ | $2.0 \times 10^{-8}$ |
| Ex. 6 | $4.5 \times 10^{-9}$ | $4.8 \times 10^{-8}$ |
| Ex. 9 | $1.5 \times 10^{-8}$ | $1.1 \times 10^{-7}$ |
| Ex. 11 | $5.8 \times 10^{-9}$ | $4.6 \times 10^{-8}$ |
| Ex. 13 | $3.0 \times 10^{-9}$ | $3.6 \times 10^{-8}$ |
| Ex. 14 | $3.6 \times 10^{-9}$ | $2.6 \times 10^{-8}$ |
| Ex. 15 | $1.4 \times 10^{-8}$ | $5.6 \times 10^{-8}$ |
| Ex. 16 | $2.8 \times 10^{-8}$ | $1.0 \times 10^{-7}$ |
| Ex. 17 | $8.8 \times 10^{-9}$ | $1.3 \times 10^{-7}$ |
| Ex. 20 | $1.7 \times 10^{-8}$ | $9.6 \times 10^{-8}$ |
| Ex. 21 | $4.8 \times 10^{-9}$ | $7.4 \times 10^{-8}$ |
| Ex. 22 | $5.1 \times 10^{-9}$ | $3.4 \times 10^{-8}$ |
| Ex. 23 | $2.2 \times 10^{-9}$ | $7.0 \times 10^{-8}$ |
| Ex. 24 | $2.5 \times 10^{-9}$ | $5.2 \times 10^{-8}$ |
| Bz. 25 | $7.0 \times 10^{-9}$ | $4.4 \times 10^{-8}$ |
| Ex. 26 | $4.2 \times 10^{-9}$ | $3.2 \times 10^{-8}$ |
| Ex. 27 | $7.7 \times 10^{-9}$ | $6.6 \times 10^{-8}$ |
| Baicalein | $4.2 \times 10^{-8}$ | $2.4 \times 10^{-6}$ |

Test Example 3

The test was conducted with a view to examining the nuclear magnetic resonance spectra and infrared absorption spectra of the compound of the first embodiment according to the present invention and the compounds for comparison.

1) Preparation of Samples

The compounds of the present invention were prepared in the same manner as in Examples 1–17 and Examples 20–29, and the compounds for comparison were prepared in the same manner as in Comparative Examples 1–9.

2) Method of the Test

The nuclear magnetic resonance spectra [$^1$H-NMR (500 MHz)] were measured in a solvent of $CDCl_3$ with a few drops of $CD_3OD$ added therein; and the infrared absorption spectra were measured according to a KBr tablet method.

3) Results of the Test

The results of the test are as shown in Tables 4–11.

TABLE 4

| Comparative example | Structural formula | $^1$H-NMR (δppm) | IR (νcm$^{-1}$) |
|---|---|---|---|
| 1 | HO-C6H4-CH=C(CN)-C6H4-Cl (3-hydroxy) | 6.95(1H, ddd), 7.27(1H, d), 7.31(1H, t), 7.43(2H, d), 7.48(1H, s), 7.60(2H, d) | 3330, 2220, 1605, 1580, 1500, 1385, 1355, 1265, 1225, 1170, 1100, 1010, 825, 790, 685 |
| 2 | HO-C6H4-CH=C(CN)-C6H4-Cl (4-hydroxy) | 6.91(2H, d), 7.40(2H, d), 7.43(1H, s), 7.57(2H, d), 7.81(2H, d) | 3340, 2230, 1615, 1590, 1520, 1490, 1440, 1410, 1380, 1350, 1280, 1260, 1235, 1200, 1180, 1115, 1100, 1015, 1000, 840, 830, 740, 720 |
| 3 | 3-CH3O,4-HO-C6H3-CH=C(CN)-C6H4-Cl | 3.96(3H, s), 6.93(1H, d), 7.38~7.42(4H, m), 7.53(1H, d), 7.57(2H, d) | 3540, 2230, 1630, 1610, 1590, 1520, 1500, 1450, 1420, 1295, 1230, 1190, 1140, 1020, 830, 800, 760 |
| 4 | 3-HO,4-CH3O-C6H3-CH=C(CN)-C6H4-Cl | 3.98(3H, s), 6.95(1H, d), 7.27(1H, dd), 7.41(2H, d), 7.43(1H, s), 7.58(2H, d), 7.73(1H, d) | 3550, 3450, 2225, 1600, 1590, 1520, 1500, 1470, 1380, 1290, 1260, 1235, 1220, 1135, 1110, 1035, 835, 830, 760 |
| 5 | 3,4-(HO)2-C6H3-CH=CH-C6H5 | 6.82(1H, d), 6.92(1H, dd), 6.92(1H, d), 6.99(1H, d), 7.06(1H, d), 7.22(1H, t), 7.34(2H, t), 7.47(2H, d) | 3400, 1595, 1520, 1450, 1390, 1365, 1300, 1265, 1205, 1155, 1110, 980, 960, 810, 750, 690 |

TABLE 5

| Comparative example | Structural formula | $^1$H-NMR (δppm) | IR (νcm$^{-1}$) |
|---|---|---|---|
| 6 | 3,4-(HO)2-C6H3-CH=C(CO2C2H5)-stilbene derivative with phenyl | 1.27(3H, t), 4.24(2H, q), 6.44(1H, d), 6.59(1H, dd), 6.66(1H, d), 7.24(2H, d), 7.33~7.46(3H, m), 7.72(1H, s) | 3480, 3230, 1680, 1600, 1590, 1520, 1460, 1445, 1380, 1340, 1290, 1250, 1195, 1160, 1115, 1040, 1025, 805, 790, 775, 705 |
| 7 | 3,4-(HO)2-C6H3-CH=C(CN)-C6H4-OH | 6.87(2H, d), 6.89(2H, d), 7.13(1H, dd), 7.28(1H, s), 7.47(2H, d), 7.58(1H, d) | 3450, 2220, 1605, 1580, 1515, 1440, 1300, 1270, 1190, 1125 |

TABLE 5-continued

| Comparative example | Structural formula | $^1$H-NMR ($\delta$ppm) | IR (vcm$^{-1}$) |
|---|---|---|---|
| 8 | (3,4-dihydroxyphenyl)–C(CN)=CH–(3,4-dihydroxyphenyl) | 6.87(1H, d), 6.89(1H, d), 7.03(1H, dd), 7.10(1H, d), 7.14(1H, dd), 7.28(1H, s), 7.56(1H, d) | 3400, 2220, 1605, 1530, 1445, 1370, 1300, 1275, 1265, 1240, 1120, 860, 800 |
| 9 | (3,4-dihydroxyphenyl)–C(CN)=CH–(4-carboxyphenyl) | 6.85(1H, d), 7.13(1H, dd), 7.19(1H, d), 7.65(1H, s), 7.95(2H, d), 8.09(2H, d) (CD$_3$OD) | 3500, 3300, 2250, 1710, 1610, 1590, 1530, 1430, 1390, 1320, 1300, 1185, 1130, 750 |

TABLE 6

| Example | Structural formula | $^1$H-NMR ($\delta$ppm) | IR (vcm$^{-1}$) |
|---|---|---|---|
| 1 | (3,4-dihydroxyphenyl)–CH=C(CN)–(4-chlorophenyl) | 6.91(1H, d), 7.17(1H, dd), 7.39(1H, s), 7.40(2H, d), 7.55(2H, d), 7.64(1H, d) | 3300, 2220, 1600, 1585, 1515, 1495, 1450, 1410, 1360, 1310, 1300, 1245, 1160, 1110, 1090, 1010, 950, 910, 830, 820, 800, 740, 715 |
| 2 | (3,4-dihydroxyphenyl)–C(CN)=CH–(4-chlorophenyl) | 6.89(1H, d), 7.09(1H, dd), 7.15(1H, d), 7.36(1H, s), 7.42(2H, d), 7.77(2H, d) | 3500, 3300, 2230, 1610, 1590, 1530, 1490, 1440, 1380, 1365, 1310, 1300, 1285, 1270, 1225, 1200, 1170, 1120, 1100, 1010, 860, 790 |
| 3 | (3,4-dihydroxyphenyl)–CH=C(CN)–(4-fluorophenyl) | 6.91(1H, d), 7.12(2H, dd), 7.15(1H, dd), 7.34(1H, s), 7.59(1H, dd), 7.64(1H, d) | 3470, 3410, 2220, 1600, 1580, 1515, 1445, 1375, 1360, 1300, 1240, 1200, 1165, 1120, 1105, 830, 800, 750, 740 |
| 4 | (3,4-dihydroxyphenyl)–CH=C(CN)–(4-bromophenyl) | 6.91(1H, d), 7.15(1H, dd), 7.40(1H, s), 7.48(2H, d), 7.55(2H, d), 7.67(1H, d) | 3300, 2225, 1620, 1600, 1585, 1515, 1490, 1450, 1410, 1360, 1300, 1280, 1245, 1170, 1120, 1080, 1005, 950, 910, 835, 820, 805, 740 |
| 5 | (3,4-dihydroxyphenyl)–CH=C(CN)–(4-K-phenyl) | 6.90(1H, d), 7.19(1H, dd), 7.36(2H, d), 7.41(1H, s), 7.62(1H, d), 7.75(2H, d) | 3370, 3220, 2230, 1585, 1520, 1485, 1450, 1400, 1375, 1290, 1245, 1195, 1120, 1065, 1000, 955, 820, 805 |

TABLE 7

| Example | Structural formula | $^1$H-NMR (δppm) | IR (vcm$^{-1}$) |
|---|---|---|---|
| 6 | 3,4-dihydroxyphenyl-CH=C(CN)-(4-methylphenyl) | 2.38(3H, s), 6.90(1H, d), 7.16(1H, dd), 7.23(2H, d), 7.38(1H, s), 7.51 (2H, d), 7.62(1H, d) | 3370, 2230, 1625, 1605, 1585, 1525, 1460, 1375, 1305, 1280, 1245, 1205, 1125, 1110, 820, 810 |
| 7 | 3,4-dihydroxyphenyl-CH=C(CN)-(3-methylphenyl) | 2.41(3H, s), 6.91(1H, d), 7.12(1H, dd), 7.17(1H, d), 7.31(1H, dd), 7.41(1H, s,), 7.42(1H, d), 7.43(1H, s), 7.71(1H, d) | 3425, 3350, 2230, 1610, 1590, 1580, 1525, 1460, 1380, 1355, 1310, 1235, 1200, 1130, 1115, 810, 775, 680 |
| 8 | 3,4-dihydroxyphenyl-CH=C(CN)-(4-methoxyphenyl) | 3.85(3H, s), 6.89(1H, d), 6.95(2H, d), 7.16(1H, dd), 7.31(1H, s), 7.55 (2H, d), 7.58(1H, d) | 3425, 3350, 2220, 1610, 1600, 1525, 1510, 1450, 1380, 1300, 1280, 1255, 1205, 1180, 1125, 1110, 1035, 1020, 865, 830 |
| 9 | 3,4-dihydroxyphenyl-CH=C(CN)-phenyl | 6.91(1H, d), 7.17(1H, dd), 7.36 (1H, t), 7.42(1H, s), 7.43(2H, t), 7.62(2H, d), 7.65(1H, d) | 3520, 3320, 2220, 1615, 1590, 1525, 1455, 1380, 1305, 1250, 1135, 760, 685 |
| 10 | 3,4-dihydroxyphenyl-CH=C(CN)-(4-trifluoromethylphenyl) | 6.93(1H, d), 7.20(1H, dd), 7.49 (1H, s), 7.68(2H, d), 7.69(1H, d), 7.74(2H, d) | 3330, 2225, 1620, 1600, 1585, 1515, 1425, 1360, 1330, 1300, 1250, 1170, 1135, 1120, 1070, 1010, 960, 920, 875, 870, 850, 810, 740 |

TABLE 8

| Example | Structural formula | $^1$H-NMR (δppm) | IR (vcm$^{-1}$) |
|---|---|---|---|
| 11 | 3,4-dihydroxyphenyl-CH=C(CN)-(4-ethylphenyl) | 1.26(3H, t), 2.68(2H, q), 6.90(1H, d), 7.14(1H, dd), 7.26(2H, d), 7.38 (1H, s), 7.54(2H, d), 7.66(1H, d) | 3400, 3260, 2950, 2240, 1605, 1590, 1530, 1445, 1395, 1385, 1315, 1290, 1240, 1210, 1120, 1110, 810, 745 |
| 12 | 3,4-dihydroxyphenyl-CH=C(CN)-(2-thienyl) | 6.86(1H, d), 7.03(1H, dd), 7.14 (1H, dd), 7.24(1H, d), 7.25(1H, s), 7.26(1H, d), 7.53(1H, d) | 3400, 2240, 1615, 1605, 1585, 1530, 1465, 1440, 1370, 1350, 1340, 1300, 1290, 1280, 1240, 1205, 1175, 1125, 1115, 825, 810, 800, 745, 700 |
| 13 | 3,4-dihydroxyphenyl-CH=C(CN)-(4-bromo-2-thienyl) | 6.90(1H, d), 7.15(1H, dd), 7.17 (1H, d), 7.20(1H, d), 7.25(1H, s), 7.57(1H, d) | 3510, 3330, 3120, 2230, 1615, 1595, 1580, 1520, 1510, 1450, 1430, 1370, 1330, 1290, 1270, 1200, 1165, 1120, 985, 900, 660, 820, 740 |

TABLE 8-continued

| Example | Structural formula | $^1$H-NMR (δppm) | IR (vcm$^{-1}$) |
|---|---|---|---|
| 14 | HO, HO — phenyl — C(CN)=CH — thiophene — Br | 6.88(1H, d), 7.02(1H, d), 7.04(1H, d), 7.14(1H, s), 7.17(1H, dd), 7.52(1H, d) | 3330, 2225, 1620, 1600, 1580, 1530, 1510, 1440, 1360, 1320, 1300, 1275, 1215, 1120, 990, 790 |
| 15 | HO, HO, HO — phenyl — CH=C(CN) — phenyl — Cl | 7.05(2H, s), 7.32(1H, s), 7.40(2H, d), 7.54(2H, d) | 3425, 2230, 1620, 1600, 1540, 1500, 1455, 1420, 1350, 1210, 1160, 1105, 1040, 825 |

TABLE 9

| Example | Structural formula | $^1$H-NMR (δppm) | IR (vcm$^{-1}$) |
|---|---|---|---|
| 16 | HO, HO — phenyl — CH=C(CN) — phenyl — CN | 6.92(1H, d), 7.26(1H, dd), 7.53(1H, s), 7.64(1H, d), 7.72(2H, d), 7.75(2H, d) | 3520, 3420, 2240, 1600, 1585, 1520, 1375, 1340, 1300, 1200, 1180, 1130, 1120, 1010, 865, 840, 810, 745 |
| 17 | HO, HO — phenyl — CH=C(CN) — phenyl — NO$_2$ · 1/4 H$_2$O | 6.93(1H, d), 7.28(1H, dd), 7.58(1H, s), 7.67(1H, d), 7.80(2H, d), 8.29(2H, d) | 3520, 3430, 2225, 1595, 1580, 1520, 1355, 1345, 1310, 1300, 1210, 1175, 1130, 860, 850, 755, 690 |

TABLE 10

| Example | Structural formula | $^1$H-NMR (δppm) | IR (vcm$^{-1}$) |
|---|---|---|---|
| 20 | HO, HO — phenyl — C(CN)=CH — phenyl | 6.90(1H, d), 7.10(1H, dd), 7.16(1H, d), 7.41(1H, t), 7.42(1H, s), 7.45(2H, t), 7.83(2H, d) | 3550, 3460, 3300, 2240, 1605, 1520, 1450, 1440, 1370, 1300, 1215, 1200, 1180, 1120, 870, 855, 790, 770, 745, 690 |
| 21 | HO, HO — phenyl — C(CN)=CH — phenyl — F | 6.89(1H, d), 7.08(1H, dd), 7.14(2H, t), 7.14(1H, d), 7.37(1H, s), 7.83(2H, dd) | 3370, 2230, 1610, 1520, 1445, 1385, 1300, 1255, 1175, 1130, 1115, 1020, 915, 860, 825, 805, 790 |

TABLE 10-continued

| Example | Structural formula | $^1$H-NMR (δppm) | IR (vcm$^{-1}$) |
|---|---|---|---|
| 22 | HO-, HO- phenyl-C(CN)=CH-phenyl-Cl (3-Cl) | 6.89(1H, d), 7.09(1H, dd), 7.15 (1H, d), 7.35(1H, s), 7.36–7.42 (2H, m), 7.75(2H, m) | 3400, 3280, 2240, 1610, 1590, 1580, 1540, 1485, 1445, 1340, 1310, 1300, 1280, 1225, 1200, 1185, 1120, 870, 810, 790, 700, 680 |
| 23 | HO-, HO- phenyl-C(CN)=CH-phenyl-Br | 6.89(1H, d), 7.09(1H, dd), 7.15 (1H, d), 7.33(1H, s), 7.58(2H, d), 7.70(2H, d) | 3550, 3300, 2245, 1610, 1590, 1530, 1490, 1440, 1410, 1385, 1370, 1300, 1240, 1210, 1200, 1180, 1135, 1080, 1010, 910, 865, 810, 785, 770 |
| 24 | HO-, HO- phenyl-C(CN)=CH-phenyl-CH$_3$ | 2.40(3H, s), 6.89(1H, d), 7.08(1H, dd), 7.14(1H, d), 7.25(1H, d), 7.38 (1H, s), 7.74(2H, d) | 3550, 3300, 2240, 1615, 1530, 1460, 1400, 1360, 1300, 1270, 1215, 1195, 1135, 910, 860, 815, 795, 790, 770, 755, 710 |

TABLE 11

| Example | Structural formula | $^1$H-NMR (δppm) | IR (vcm$^{-1}$) |
|---|---|---|---|
| 25 | HO-, HO- phenyl-C(CN)=CH-phenyl-CH$_3$ (3-CH$_3$) | 2.38(3H, s), 6.86(1H, d), 7.06(1H, dd), 7.13(1H, d), 7.20 (1H, d), 7.32(1H, I), 7.37(1H, s), 7.60(1H, s), 7.63(1H, d) | 3470, 3300, 2230, 1625, 1610, 1600, 1580, 1530, 1520, 1475, 1440, 1360, 1295, 1275, 1250, 1220, 1200, 1125, 1110, 850, 810, 790, 775, 740, 680 |
| 26 | HO-, HO- phenyl-C(CN)=CH-phenyl-C$_2$H$_5$ | 1.26(3H, I), 2.70(2H, q), 6.89(1H, d), 7.09(1H, dd), 7.15 (1H, d), 7.28(2H, d), 7.39(1H, s), 7.76(2H, d) | 3470, 3180, 2990, 2950, 2260, 1620, 1520, 1475, 1400, 1370, 1340, 1300, 1230, 1215, 1115, 1065, 1030, 930, 905, 885, 835, 815, 795, 695 |
| 27 | HO-, HO- phenyl-C(CN)=CH-thienyl-CH$_3$ | 2.55(3H, s), 6.78(1H, d), 6.86(1H, d), 7.03(1H, dd), 7.09 (1H, d), 7.34(1H, d), 7.44(1H, s) | 3540, 3300, 2225, 1620, 1605, 1590, 1530, 1520, 1455, 1385, 1360, 1315, 1290, 1240, 1215, 1200, 1180, 1130, 1120, 1060, 1020, 875, 810, 790, 745 |
| 28 | HO-, HO- phenyl-C(CN)=CH-furyl-CH$_3$ | 2.39(3H, s), 6.17(1H, d), 6.87(1H, d), 6.98(1H, d), 7.03(1H, dd), 7.09(1H, d), 7.16(1H, s) | 3480, 3280, 3240, 2230, 1625, 1610, 1515, 1445, 1390, 1370, 1355, 1310, 1295, 1280, 1245, 1225, 1205, 1185, 1130, 1115, 1035, 865, 860, 790, 740 |
| 29 | HO-, HO- phenyl-CH=C(CN)-furyl-CH$_3$ | 2.36(3H, s), 6.07(1H, d), 6.45(1H, d), 6.88(1H, d), 7.13(1H, dd), 7.34 (1H, s), 7.56(1H, d) | 3300, 2230, 1605, 1580, 1515, 1380, 1305, 1260, 1120, 1025, 800, 780, 740 |

Comparative Example 1

The yellow crystalline compound, 551 mg (yield: 43.1%), represented by the following formula were obtained according to the same procedure as in Example 1 except that 611 mg (5.0 mmole) of 3-hydroxybenzaldehyde (purchased from Tokyo Kasei) were used instead of 3,4-dihydroxybenzaldehyde:

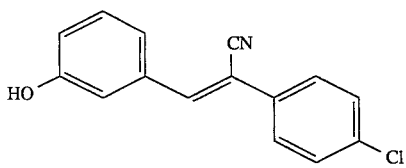

Formula 28

The melting point of the obtained compound was 114.5° to 116.5° C.

Comparative Example 2

The yellow crystalline compound, 975 mg (yield: 76.2%), represented by the following formula were obtained according to the same procedure as in Example 1 except that 611 mg (5.0 mmole) of 4-hydroxybenzaldehyde (purchased from Tokyo Kasei) were used instead of 3,4-dihydroxybenzaldehyde:

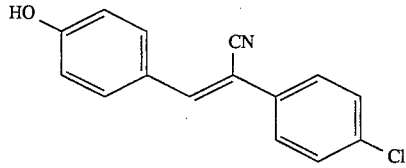

Formula 29

The melting point of the obtained compound was 200° to 202° C.

Comparative Example 3

The pale yellow crystalline compound, 488 mg (yield: 97.6%), represented by the following formula were obtained according to the same procedure as in Example 1 except that 761 mg (5.0 mmole) of 3-hydroxy-4-methoxybenzaldehyde (purchased from Jansen) were used instead of 3,4-dihydroxybenzaldehyde:

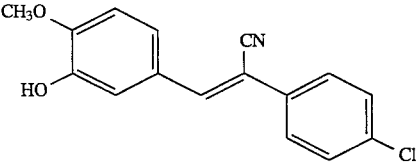

Formula 30

The melting point of the obtained compound was 139° to 140° C.

Comparative Example 4

The yellow crystalline compound, 481 mg (yield: 68.7%), represented by the following formula were obtained according to the same procedure as in Example 1 except that 761 mg (5.0 mmole) of 4-hydroxy-3-methoxybenzaldehyde (purchased from Tokyo Kasei) were used instead of 3,4-dihydroxybenzaldehyde:

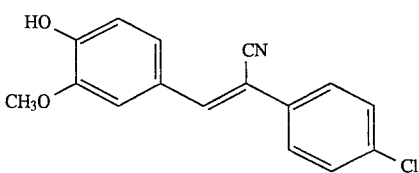

Formula 31

The melting point of the obtained compound was 122° to 123° C.

Comparative Example 5

To a suspension of benzyltriphenylphosphonium bromide (4.33 g, 10 mmol, purchased from Lancaster) in 12 ml of tetrahydrofuran (purchased from Aldrich) was added a solution of lithium bistrimethylsilylamide (1.0M solution in tetrahydrofuran, 10 ml, purchased from Aldrich) at room temperature and the mixture was stirred further for 30 minutes. To the mixture was added a solution of 3,4-dimethoxybenzaldehyde (1.5 g, 9 mmol, purchased from Tokyo Kasei) in 6 ml of tetrahydrofuran and the resultant mixture was stirred for additional 2.5 hours. The reaction was quenched by the addition of methanol. A crude product obtained after an ordinary treatment was subjected to chromatography on silica gel to give a mixture of trans- and cis-isomers of 3,4-dimethoxystilbene. The mixture was recrystalized from hexane-ethyl acetate (30:1) to give 680 mg (yield: 31.0%) of the trans isomer.

A mixture of 222 mg (0.93 mmole) of the above-mentioned trans-3,4-dimethoxystilbene and 1.5 g (13 mmole) of pyridinium chloride (purchased from Wako Junyaku Kogyo) was melted and stirred at 200° C. in an atmosphere of argon gas for 45 minutes, air-cooled, treated with 50 ml of 2N hydrochloric acid, extracted with ethyl acetate, washed with saturated saline and dried over anhydrous magnesium sulfate. The solvent was evaporated under reduced pressure, and the residue was subjected to thin-layer chromatography (ethyl acetatehexane=1:1) to obtain 100 mg (yield: 50.0 %) of a white crystalline compound represented by the following formula:

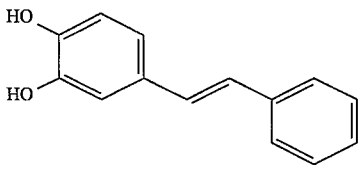

Formula 32

The melting point of the obtained compound was 170° to 171° C.

Comparative Example 6

To a mixture of ethyl phenylacetate (821 mg, 5.0 mmol, purchased from Tokyo Kasei) and 3,4-dihydroxybenzaldehyde (691 mg, 5.0 mmol, purchased from ToKyo Kasei) in 10 ml of ethanol was added 0.54 ml of piperidine (purchased from Wako Junyaku Kogyo) and refluxed for 24 hours. After being cooled, the mixture was poured into 100 ml of 1N-hydrochloric acid. The precipitate was collected and washed with water, then dissolved in ethyl acetate. The solution was washed with 20% aqueous sodium bisulfite solution twice and then with brine. The organic layer was dried over anhydrous sodium sulfate. The solvent was removed under reduced pressure. The residue was purified by column chromatography on silica gel. Elution with hexane-ethyl acetate (10:1–10:4) gave 499 mg (yield: 35.1%) of the product represented by the following formula as a yellow cristalline:

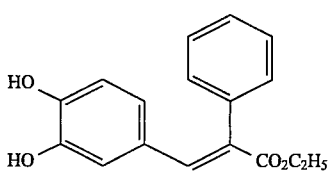

Formula 33 melting point (hereinafter described as mp)153°–154.5° C.

Comparative Example 7

The α-cyano-3',4,4'-trimethoxystylbene (white crystal), 2.61 g (yield: 88.0%), were obtained according to the same procedure as in Example 2 except that 1.47 g (10 mmole) of 4-methoxyphenylacetonitrile (purchased from Aldrich) were used instead of 3,4-dimethoxyphenylacetonitrile and that 1.66 g (10 mmole) of 3,4-dimethoxybenzaldehyde (purchased from Tokyo Kasei) were used instead of 4-chlorobenzaldehyde.

The yellow crystals, 588 mg (yield: 93.0%), represented by the following formula were obtained according to the same procedure as in Example 2 except that 0.74 g (2.5 mmole) of the above-mentioned α-cyano-3',4,4'-trimethoxystilbene and 3.47 g (30 mmole) of pyridinium chloride (purchased from Wako Junyaku Kogyo) were used:

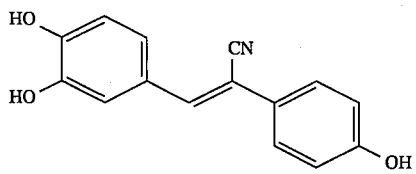

Formula 34

The melting point of the obtained compound was 229° to 231° C.

Comparative Example 8

The α-cyano-3,3',4,4'-tetramethoxystilbene (yellow crystal), 2.99 g (yield: 92.0%), were obtained according to the same procedure as in Example 2 except that 1.66 g (10 mmole) of 3,4-dimethoxybenzaldehyde (purchased from Tokyo Kasei) were used instead of 4-chlorobenzaldehyde.

The yellow crystals, 138 mg (yield: 20.5%), represented by the following formula were obtained according to the same procedure as in Example 2 except that 0.81 g (2.5 mmole) of the above-mentioned α-cyano-3',3,4,4'-tetramethoxystilbene and 3.47 g (30 mmole) of pyridinium chloride (purchased from Wako Junyaku Kogyo) were used:

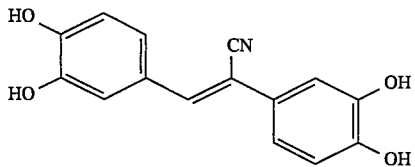

Formula 35

The melting point of the obtained compound was 238° to 239° C.

Comparative Example 9

A mixture of 3,4-dimethoxyphenylacetonitrile (475 mg, 2.68 mmol, purchased from Tokyo Kasei) and 4-formylbenzoic acid (402 mg, 2.68 mmol, purchased from Tokyo Kasei) was heated to dissolve in 5 ml of anhydrous ethanol. To the mixture was added a solution of sodium ethoxide (2.68M in denatured alcohol, 2 ml, purchased from Aldrich) and the mixture was allowed to stand for 1 hour. To the mixture was added 30 ml of water and the mixture was stirred. Insoluble material was collected and washed with water then treated with 30 ml of 2N-hydrochloric acid. The precipitate was collected and washed with water thoroughly to give 605 mg (yield: 70.3%) of α'-cyano-3',4'-dimethoxy-4-stilbenecarboxylic acid as a yellow crystalline compound.

A mixture of the above mentioned α'-cyano-3',4'-dimethoxy-4-stilbenecarboxylic acid (309 mg, 1.0 mmol) and pyridinium chloride (1.73 g, 15 mmol, purchased from Wako Junyaku Kogyo) was melted and stirred at 200° C. in an atmosphere of argon gas for one hour. After being cooled, to the resultant mass was added 2N-hydrochloric acid and the mass was crushed and stirred. The precipitate was collected and washed with water, then taken up in ethanol. The solvent was removed under reduced pressure and the residue was recrystalized from ethanol-hexane to give 198 mg (yield: 70.4%) of the product represented by the following formula:

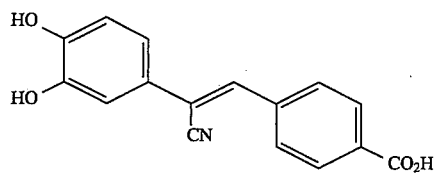

Formula 36 as a yellow crystalline, mp 285°–287° C.

Test Example 4

The test was conducted with a view to examining the 12-lipoxgenase inhibitory effect of the compound formed from the compound of the third embodiment according to the present invention being absorbed in vivo and then deacylated.

1) Preparation of Enzyme Solution

It was prepared according to the same procedure as in Test Example 1.

2) Method of Measurement of Enzyme Activity

Measurement was performed according to the same procedure as in Test Example 1.

3) Results of the Test

The results of the test are as shown in Table 12. In Table 12 were contrasted the 12-lipoxgenase $IC_{50}$ values of the compounds formed from the compounds of Examples 30–39, 43, 45 and 48 of the present invention being absorbed in vivo and then deacylated with that of baicalein (purchased from Wako Junyaku Kogyo), a known compound, for comparison.

As is apparent from Table 12, it was revealed that the 12-lipoxgenase inhibitory effect of the compound of each Example according to the present invention is far more excellent than that of baicalein. Incidentally, as a result of per forming a test upon other compounds of the present invention, almost the same results were obtained.

TABLE 12

| Compounds of the invention (acyl compound) | Deacylated compounds | 12-Lipoxygenase * inhibitory effect of deacylated compounds |
|---|---|---|
| Ex. 1 (Formula 34b) | Ref. Ex. 1 (Formula 32b) | $4.2 \times 10^{-9}$ (M) |
| Ex. 2 (Formula 35b) | Ref. Ex. 1 (Formula 32b) | $4.2 \times 10^{-9}$ |
| Ex. 3 (Formula 36b) | Ref. Ex. 1 (Formula 32b) | $4.2 \times 10^{-9}$ |
| Ex. 4 (Formula 37b) | Ref. Ex. 1 (Formula 32b) | $4.2 \times 10^{-9}$ |

TABLE 12-continued

| Compounds of the invention (acyl compound) | Deacylated compounds | 12-Lipoxygenase * inhibitory effect of deacylated compounds |
|---|---|---|
| Ex. 5 (Formula 39b) | Ref. Ex. 5 (Formula 38b) | $1.8 \times 10^{-9}$ |
| Ex. 6 (Formula 40b) | Ref. Ex. 3 (Formula 33b) | $5.1 \times 10^{-9}$ |
| Ex. 7 (Formula 42b) | Ref. Ex. 7 (Formula 41b) | $4.8 \times 10^{-9}$ |
| Ex. 8 (Formula 44b) | Ref. Ex. 8 (Formula 43b) | $3.6 \times 10^{-9}$ |
| Ex. 9 (Formula 46b) | Ref. Ex. 9 (Formula 45b) | $5.4 \times 10^{-9}$ |
| Ex. 10 (Formula 48b) | Ref. Ex. 10 (Formula 47b) | $4.5 \times 10^{-9}$ |
| Ex. 14 (Formula 56b) | Ref. Ex. 14 (Formula 55b) | $6.0 \times 10^{-9}$ |
| Ex. 16 (Formula 60b) | Ref. Ex. 16 (Formula 59b) | $8.8 \times 10^{-9}$ |
| Ex. 19 (Formula 66b) | Ref. Ex. 19 (Formula 65b) | $3.0 \times 10^{-9}$ |
| Baicalein | | $4.2 \times 10^{-8}$ |

Note
*: $IC_{50}$ values

Test Example 5

The test was performed to examine whether or not deacylated compounds would be formed due to esterases present in the enzyme solution when the compounds in the third embodiment according to the present invention were treated with the same enzyme solution as in Test Example 4.

1) Preparation of Enzyme Solution

The enzyme solution was prepared according to the same procedure as described in Test Example 4.

2) Method of the Test

One ml of the above mentioned enzyme solution was diluted with 11 ml of a resuspension buffer. To an aliquot (300 μl) of this enzyme solution was added 3 μl of a $1.0 \times 10^{-3}$ M test compound solution in dimethyl sulfoxide. The mixture was incubated at 37° C. for an indicated time, then the reaction was ceased by the addition of 1 ml of acetonitrile. Twenty μl of the above mixture was subjected to reverse phase high-performance liquid chromatography equipped with a C-18 column to quantify the amount of deacylated products. As a control, a test using 300 μl of the resuspension buffer solution mentioned above instead of the enzyme solution was also performed.

Conditions of reverse phase high-performance liquid chromatography:

Column: Superspher RP-18(e) (purchased from Merck), 4.0 mm in diameter, 125 mm in length Flow velocity: 1.0 ml/minute Eluent: Acetonitrile containing 50 mM $NaClO_4$ and 50 mM orthophosphate-water (55: 45)

Column temperature: 30° C.

Calibration: Absorbance of 280 nm

3) Results of the Test

The results of the test upon the compounds of Example 30 (Formula 34b) and Example 31 (Formula 35b) of the compounds according to the present invention will be shown. Since both the compounds of Example 30 (Formula 34b) and Example 31 (Formula 35b) are thought to be converted into the compound of Referential Example 1 (Formula 32b) through deacylation, the retention time of the compound of Referential Example 1 was checked strictly under the employed conditions with reverse phase high-performance liquid chromatography mentioned above (retention time: 4.06 minutes) and a calibration curve of the compound was made using authentic sample of Referential Example 1.

As a case of using the resuspension buffer instead of the enzyme solution, no deacylated compound (Formula 32b) was formed from both compounds of Example 30 (Formula 34b) and Example 31 (Formula 35b).

When the similar test was performed using the above enzyme solution, the both compounds were deacylated with increasing times, and the deacylated compound was observed in the reaction solution as shown in Table 13.

These results clearly revealed that in the compounds of the present invention, modified moieties are cleaved relatively rapidly to form deacylated compound when contacted with an enzyme solution (maybe containing a kind of esterase in addition to 12-lipoxygenase) prepared from rat platelets.

On the other hand, the compounds formed through deacylation revealed a remarkably strong inhibitory activity against 12-lipoxgenase as shown in Test Example 4. The compounds described in the present invention were regarded as precursors to form compounds having inhibitory effect on 12-lipoxgenase and can be there#ore utilized as so-called pro-drugs.

Although other compounds in the present invention were also tested, almost the same results were obtained.

TABLE 13

| | Reaction time (min.) | |
|---|---|---|
| Compound | 30 | 60 |
| Formula 34b | 70.9 | 82.8 |
| Formula 35b | 56.5 | 64.6 |

Note: The numerical values show the conversion (%) from Formula 34b or Formula 35b to Formula 32b.

Test Example 6

The test was conducted with a view to examining the 12-lipoxygenase and 5-lipoxygenaee inhibitory effects of the compounds of the fifth embodiment according to the present invention.

1. Preparation of Samples

1) Samples

Samples were prepared according to the same procedure as in Examples 54–58 to be described later. Incidentally, as a control was used baicalein (purchased from Wako Junyaku Kogyo), a known compound represented by the following formula 21c:

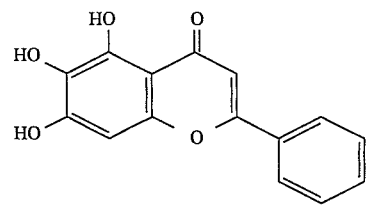

Formula 21c

2) Preparation of 12-Lipoxygenase Enzyme Solution

It was prepared according to the same procedure as in Test Example 1.

2) Preparation of 5-Lipoxygenase Enzyme Solution

It was prepared according to the same procedure as in Test Example 2.

2. Method of the Test

1) Method of Measurement of 12-Lipoxygenase Enzyme Activity

The measurement was performed according to the same procedure as in Test Example 1.

2) Method of Measurement of 5-Lipoxygenase Enzyme Activity

The measurement was performed according to the same procedure as in Test Example 2.

3) Measurement of Enzyme Activities

The enzyme activities of the compounds of the present invention prepared according to the same procedure as in Examples 54–58 to be described later and baicalein as sample substances at varied concentrations were measured according to the above-mentioned method, and mole concentrations showing 50% 12-lipoxgenase and 5-lipoxgenase inhibition ratios (hereinafter may be described as $IC_{50}$ values) were obtained from the measured values of the sample substances.

3. Results of the Test

The results of the test are as shown in Table 23. As is apparent from Table 23, a remarkably strong inhibitory effect to 12-lipoxygenase was recognized in the compounds of the present invention, and $IC_{50}$ values were of the order of $10^{-9}$ moles, which were equivalent to that of known baicalein or more. On the other hand, the compounds of the present invention have an inhibitory effect also to 5-lipoxgenase; and the $IC_{50}$ values thereof were 3 to 30 times or more those to 12-lipoxygenase. Thus, it was revealed that the compounds of the present invention have an inhibitory effect to 12-lipoxygenase selectively.

TABLE 23

| Compound | 12-Lipoxygenase inhibitory effect $IC_{50}$ (M) | 5-Lipoxygenase inhibitory effect $IC_{50}$ (M) |
| --- | --- | --- |
| Formula 22c (Example 54) | $8.6 \times 10^{-9}$ | $5.6 \times 10^{-8}$ |
| Formula 23c (Example 55) | $1.0 \times 10^{-8}$ | $3.0 \times 10^{-8}$ |
| Formula 24c (Example 56) | $5.6 \times 10^{-9}$ | $2.8 \times 10^{-8}$ |
| Formula 25c (Example 57) | $5.9 \times 10^{-9}$ | $3.6 \times 10^{-8}$ |
| Formula 26c (Example 58) | $3.2 \times 10^{-9}$ | $3.4 \times 10^{-8}$ |
| Formula 21c Baicalein | $4.2 \times 10^{-8}$ | $2.4 \times 10^{-6}$ |

BEST EMBODIMENT FOR CARRYING OUT THE INVENTION

Next, the present invention will be described in detail according to Examples and Referential Examples; the present invention is restricted to the following Examples by no means.

EXAMPLE 1

To a mixture of 4- chlorophenylacetonitrile (758 mg, 5.0 mmol, purchased from Tokyo Kasei,) and 3,4-dihydroxybenzaldehyde (691 mg, 5.0 mmol, purchased from Tokyo Kasei) in 10 ml of ethanol was added 0.54 ml of piperidine (purchased from wako Junyaku Kogyo) and refluxed for 6 hours. After being cooled, the mixture was poured into 100 ml of 1N-hydrochloric acid and stirred. The precipitate was collected and washed with water, then dissolved in ethyl acetate. The solution was washed with 20% aqueous sodium bisulfite solution twice and then with brine. The organic layer was dried over anhydrous sodium sulfate. The solvent was removed under reduced pressure. The residue was purified by column chromatography on silica gel. Elution with hexane-ethyl acetate (5:1–5:2) gave 919 mg (yield: 67.6%) of the product represented by the following formula:

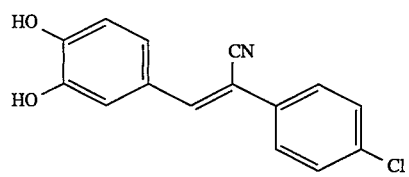

Formula 37 as a yellow crystalline, mp 160°–162° C.

EXAMPLE 2

A mixture of 3,4-dimethyoxyphenylacetonitrile (1.77 g, 10.0 mmol, purchased from Tokyo Kasei,) and 4-chlorobenzaldehyde (1.4 g, 10.0 mmol, purchased from Tokyo Kasei) in 5 ml of ethanol was heated to dissolve. Two drops of 20% aqueous sodium hydroxide solution was then added and the reaction mixture was stirred over night. The resultant reaction mass was crushed in ethanol. The precipitate was Collected and washed with ethanol then with hexane, and dried to give 2.39 g (yield: 79.7%) of α-cyano-3,4-dimethoxy-4'-chlorostilbene as a greenish yellow crystalline.

A mixture of the above α-cyano-3,4-dimethoxy-4'-chlorostilbene (0.75 g, 2.5 mmol) and pyridinium chloride (2.31 g, 20.0 mmol, purchased from Wako Junyaku Kogyo,) was melted to mix on an oil bath (210° C.) under atmosphere of argon gas. Stirring was continued for additional one hour. After being cooled, to the resultant reaction mass were added 2N-hydrochloric acid and ethyl acetate. The organic layer was separated and the water layer was extracted with ethyl acetate. The combined organic layer was washed with brine and then dried over anhydrous sodium sulfate. The solvent was evaporated under reduced pressure. The residue was dissolved in a small amount of ethyl acetate. Then hexane was added to the solution till the mixture became slightly cloudy and the mixture was stirred. The precipitate was collected and dried to give 455 mg (yield: 67.0%) of the product represented by the following formula:

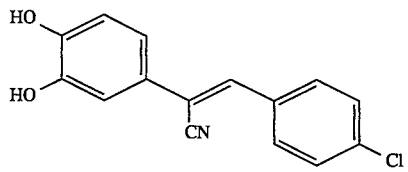

Formula 38 as a yellow crystalline, mp 171°–172° C.

EXAMPLE 3

The light yellow crystalline compound, 405 mg (yield: 31.7%), represented By the following formula were obtained according to the same procedure as in Example 1 except that 676 mg (5.0 mmole) of 4-fluorophenylacetonitrile (purchased from Tokyo Kasei) were used instead of 4-chlorophenylacetonitrile:

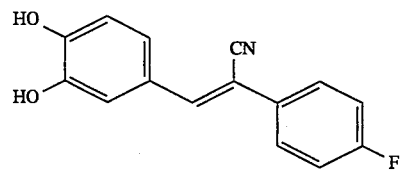

Formula 39

The melting point of the obtained compound was 184° to 186° C.

EXAMPLE 4

The light yellow crystalline compound, 1.14 g (yield: 72.2%), represented by the following formula were obtained according to the same procedure as in Example 1 except that 980 mg (5.0 mmole) of 4-bromophenylacetonitrile (purchased from Tokyo Kasei) were used instead of 4-chlorophenylacetonitrile:

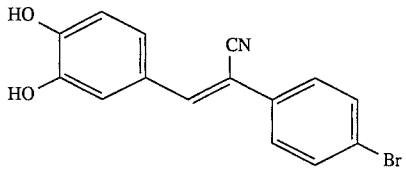

Formula 40

The melting point of the obtained compound was 172° to 175° C.

EXAMPLE 5

The yellow crystalline compound, 1.39 g (yield: 76.4%), represented By the following formula were obtained according to the same procedure as in Example 1 except that 1.22 g (5.0 mmole) of 4-iodophenylacetonitrile synthesized according to the method below were used instead of 4-chlorophenylacetonitrile:

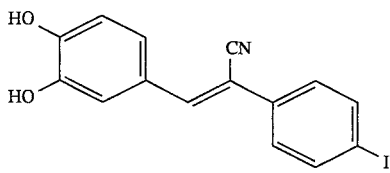

Formula 41

The melting point of the obtained compound was 197° to 198° C.

[synthesis of 4-Iodophenylacetonitrile]

A mixture of p-iodotoluene (4.36 g, 20 mmol, purchased from Toko Kasei) and N-bromoeuccinimide (3.92 g, 2 mmol, purchased from Tokyo Kasei) in 60 ml of carbontetrachloride (purchased from Wako Junyaku Kogyo) was refluxed for 4 hours under irradiation by means of an incandescent lamp to give 2.67 g (yield: 45.0%) of 4-iodobenzyl bromide as a white crystalline.

To a hot solution (50° C.) of sodium cyanide 0.49 g, 10.0 mmom, purchased from Kokusan Kagaku) in 10 ml of dimethyl sulfoxide (purchased from Aldrich) was added the above 4-iodobenzyl bromide (1.48 g, 5.0 mmol) and the mixture was stirred for three hours at ambient temperature. To the resultant reaction mass was added water and extracted with hexane. The solvent was removed to give 0.84 g (yield: 68.9%) of 4-iodophenylacetonitrile as a white crystalline.

EXAMPLE 6

The yellow crystalline compound, 515 mg (yield: 41.0%), represented by the following formula were obtained according to the same procedure as in Example 1 except that 656 mg (5.0 mmole) of p-tolylacetonitrile (purchased from Tokyo Kasei) were used instead of 4-chlorophenylacetonitrile:

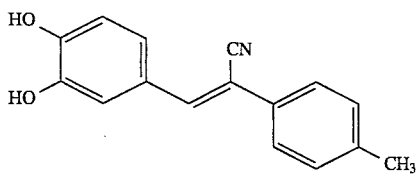

Formula 42

The melting point of the obtained compound was 164° to 165° C.

EXAMPLE 7

The light yellow crystalline compound, 360 mg (yield: 28.7%), represented by the following formula were obtained according to the same procedure as in Example 1 except that 656 mg (5.0 mmole) of m-tolylacetonitrile (purchased from Aldrich) were used instead of 4-chlorophenylacetonitrile:

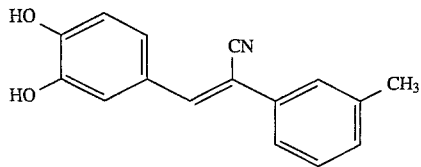

Formula 43

The melting point of the obtained compound was 144° to 145 ° C.

EXAMPLE 8

The light yellow crystalline compound, 214 mg (yield: 16.0%), represented by the following formula were obtained according to the same procedure as in Example 1 except that 736 mg (5.0 mmole) of 4-methoxyphenylacetonitrile (purchased from Aldrich) were used instead of 4-chlorophenylacetonitrile:

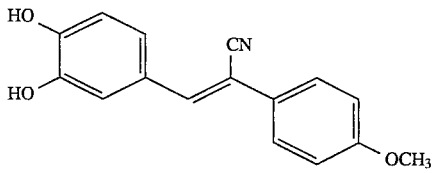

Formula 44

The melting point of the obtained compound was 197° to 198° C.

EXAMPLE 9

The light yellow crystalline compound, 890 mg (yield: 75.0%), represented by the following formula were obtained according to the same procedure as in Example 1 except that 586 mg (5.0 mmole) of phenylacetonitrile (purchased from Tokyo Kasei) were used instead of 4-chlorophenylacetonitrile:

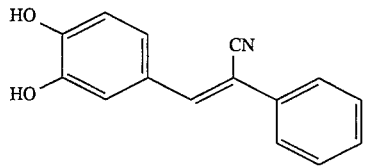

Formula 45

The melting point of the obtained compound was 148° to 150° C.

EXAMPLE 10

The yellow crystalline compound, 657 mg (yield: 87.4%), represented by the following formula were obtained according to the same procedure as in Example 1 except that 926 mg (5.0 mmole) of 4-trifluoromethylphenylacetonitrile (purchased from Aldrich) were used instead of 4-chlorophenylacetonitrile:

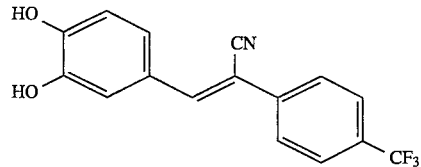

Formula 46

The melting point of the obtained compound was 168° to 169° C.

EXAMPLE 11

The light yellow crystalline compound, 281 mg (yield: 21.2%), represented by the following formula were obtained according to the same procedure as in Example 1 except that 726 mg (5.0 mmole) of 4-ethylphenylacetonitrile synthesized according to the method below were used instead of 4-chlorophenylacetonitrile:

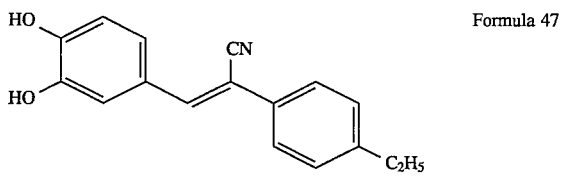

Formula 47

The melting point of the obtained compound was 137° to 138° C.

[Synthesis of 4-Ethylphenylacetonitrile]

A mixture of 4-ethylbenzyl alcohol (2.72 g, 20 mmol, purchased from Aldrich) and 50 ml of 47% hydrobromic acid (purchased from Wako Junyaku Kogyo) was stirred vigorously for 30 minutes at room temperature. The reaction mixture was extracted with hexane to give 3.98 g of 4-ethylbenzyl bromide as a colorless oil. Then to a hot solution (50° C.) of sodium cyanide (1.96 g, 40 mmol) in 20 ml of dimethyl sulfoxide was added the above 3.98 g of 4-ethylbenzyl bromide and the mixture was stirred for 3 hours at ambient temperature. To the resultant reaction mass was added water and extracted with hexane. The solvent was removed to give 2.70 g (yield: 93.1%) of 4-ethylphenylacetonitrile as a pale yellow oil.

EXAMPLE 12

The yellow crystalline compound, 281 mg (yield: 21.2%), represented by the following formula were obtained according to the same procedure as in Example 1 except that 616 mg (5.0 mmole) of thiophene-2-ylacetonitrile (purchased from Tokyo Kasei) were used instead of 4-chlorophenylacetonitrile:

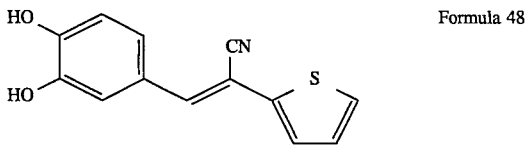

Formula 48

The melting point of the obtained compound was 180.5° to 181.5° C.

EXAMPLE 13

The yellow crystalline compound, 1.05 g (yield: 65.0%), represented by the following formula were obtained according to the same procedure as in Example 1 except that 1.01 g (5.0 mmole) of 4-bromothiophene-2-ylacetonitrile synthesized according to the method below were used instead of 4-chlorophenylacetonitrile:

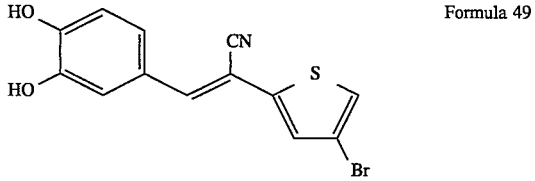

Formula 49

The melting point of the obtained compound was 222° to 224° C.

[Synthesis of 4-Bromothiophene-2-Ylacetonitrile]

To a solution of 4-bromothiophene-2-carboxaldehyde (9.55 g, 50 mmol, purchased from Aldrich) in 100 ml of ethanol was added sodium borohydride (3.78 g, 100 mmol purchased from Yoneyama Yakuhin) gradually under cooling in an ice bath. After the completion of addition, the mixture was stirred further for 1.5 hours at room temperature. The reaction mixture was acidified with hydrochlorid acid, then was concentrated to dryness under reduced pressure. To the residue was added water and extracted with ether to give 9.29 g (yield: 96%) of 4-bromothiophen-2-ylmethanol as in oil.

A mixture of the above 4-bromothiophen-2-ylmethanol (4.83 g, 25 mmol) and 63 ml of 47% hydrobromic acid was stirred vigorously for 30 minutes at room temperature. The reaction mixture was extracted with pentane to give 5.31 g (yiel: 82.8%) of 2-bromomethyl-4-bromothiophene as a pale yellow oil. Thus obtained 5.12 g of 2-bromomethyl-4-bromothiophene was reacted with sodium cyanide according to the same procedure as in the synthesis of 4-iodophenylacetonitrile of example 5 to give 1.50 g (yield: 37.0%) of 4-bromothiophen-2-ylacetonitrile as a white crystal, removing by-product of α,α-bis[(4-bromothiophen-2-yl)methyl]-4-bromothipheneaetonitrile by means of recrystalization.

EXAMPLE 14

The yellow crystalline compound, 216 mg (yield: 13.4%), represented by the following formula were obtained according to the same procedure as in Example 1 except that 1.01 g (5.0 mmole) of 5-bromothiophen-2-ylacetonitrile synthesized according to the method below were used instead of 4-chlorophenylacetonitrile:

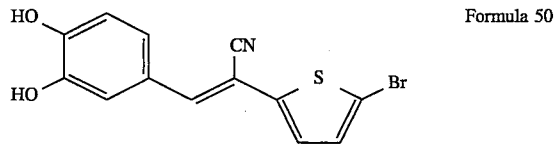

Formula 50

The melting point of the obtained compound was 185° to 186° C.

[Synthesis of 5-Bromothiophene-2-Ylacetonitrile]

This compound was synthesized according to the same method as that of synthesis of 4-bromothiophen-2-ylacetonitrile of Example 13 except that 5-bromothiophene-2-carboxaldehyde (purchased from Aldrich) was used and that purification was performed according to high-performance liquid chromatography.

EXAMPLE 15

The light yellow crystalline compound, 344 mg (yield: 23.9%), represented by the following formula were obtained according to the same procedure as in Example 1 except that 771 mg (5.0 mmole) of 3,4,5-trihydroxybenzaldehyde (purchased from Aldrich) were used instead of 3,4-dihydroxybenzaldehyde:

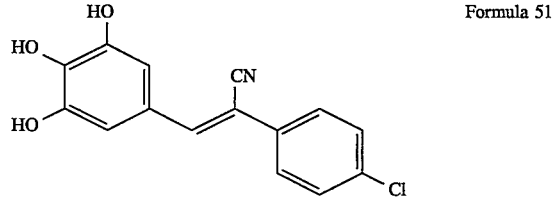

Formula 51

The melting point of the obtained compound was 240° to 243° C.

EXAMPLE 16

The yellow crystalline compound, 558 mg (yield: 85.1%), represented by the following formula were obtained according to the same procedure as in Example 1 except that 355 mg (2.5 mmole) of cyanophenylacetonitrile synthesized according to the method below instead of 4-chlorophenylacetonitrile, 345 mg (2.5 mmole) of 3,4-dihydroxybenzaldehyde (purchased from Aldrich), 5 ml of ethanol and 0.27 ml of piperidine (purchased from Wako Junyaku Kogyo) were used and that the reaction product was stirred at room temperature for 6 hours:

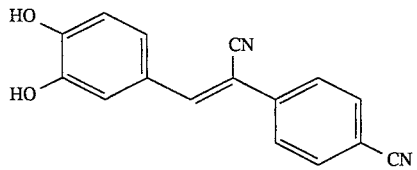

Formula 52

The melting point of the obtained compound was 263° to 265° C.

[Synthesis of Cyanophenylacetonitrile]

4-bromomethylbenzonitrile (white crystal), 2.0 g (yield: 51.0%), were obtained according to the same method as that of synthesis of 4-iodophenylacetonitrile of Example 5 except that 2.34 g (20 mmole) of p-tolunitrile (purchased from Tokyo Kasei) were used. Subsequently, 438 mg (yield: 34.2%) of light yellow crystals of 4-cyanophenylacetonitrile were obtained according to the same method as that of synthesis of 4-iodophenylacetonitrile of Example 5 except that 1.76 g (9.0 mmole) of the above 4-bromomethylbenzonitrile were used and that purification was performed according to silica gel column chromatography and recrystallization.

EXAMPLE 17

The orange crystalline compound, 1.18 g (yield: 82.3%), represented by the following formula were obtained according to the same procedure as in Example 1 except that 811 mg (5.0 mmole) of 4-nitrophenylacetonitrile (purchased from Aldrich) were used instead of 4-chlorophenylacetonitrile, that the reaction product was stirred at room temperature and that purification was performed according to recrystallization from ethanol-water:

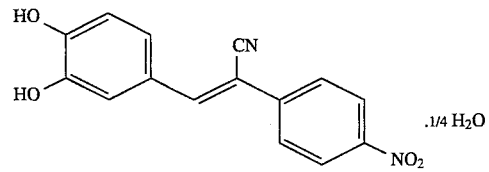

Formula 53

.1/4 H₂O

The melting point of the obtained compound was 260° to 262° C.

EXAMPLE 18

A mixture with the following composition per tablet was prepared and tableted by means of a tabletor according to an ordinary manner to produce a medicine of the present invention.

| | |
|---|---|
| Compound obtained in Example 1 | 30.0 (mg) |
| Lactose (purchased from Iwaki Seiyaku) | 40.0 |
| Cornstarch (purchased from Yoshida Seiyaku) | 15.0 |
| Magnesium stearate (purchased from Taihei Kagaku) | 0.4 |
| Carboxymethyl cellulose calcium (purchased from Nichirin Kagaku Kogyo) | 20.0 |

EXAMPLE 19

A mixture with the following composition per capsule was prepared and put into a gelatin capsule according to an ordinary manner to produce a medicine of the present invention.

| | |
|---|---|
| Compound obtained in Example 1 | 30.0 (mg) |
| Lactose (purchased from Iwaki Seiyaku) | 40.0 |
| Finely powdered cellulose (purchased from Nippon Soda) | 30.0 |
| Magnesium stearate (purchased from Taihei Kagaku) | 3.0 |

EXAMPLE 20

The α-cyano-3,4-dimethoxystilbene (yellow crystal), 2.62 g (yield: 98.9%), were obtained according to the same procedure as in Example 2 except that 1.06 g (10.0 mmole) of benzaldehyde (purchased from Wako Junyaku Kogyo) were used instead of 4-chlorobenzaldehyde.

The yellow crystalline compound, 253 mg (yield: 53.4%), represented by the following formula were obtained according to the same procedure as in Example 2 except that 531 mg (2.0 mmole) of the above α-cyano-3,4-dimethoxystilbene were used instead of α-cyano-3,4-dimethoxy-4'-chlorostilbene:

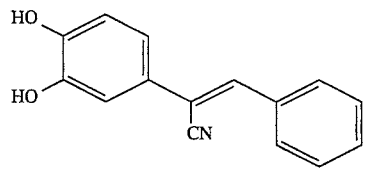

Formula 54

The melting point of the obtained compound was 172.5° to 173.0° C.

EXAMPLE 21

The α-cyano-3,4-dimethoxyfluorostilbene (white crystal), 2.33 g (yield: 82.2%), were obtained according to the same procedure as in Example 2 except that 1-24 g (10.0 mmole) of 4-fluorobenzaldehyde (purchased from Tokyo Kasei) were used instead of 4-chlorobenzaldehyde.

The white crystalline compound, 432 mg (yield: 84.6%), represented by the following formula were obtained according to the same procedure as in Example 2 except that 567 mg (2.0 mmole) of the above α-cyano-3,4-dimethoxy-4'-fluorostilbene were used instead of α-cyano-3,4-dimethoxy-4'-chlorostilbene:

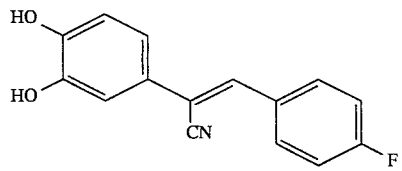

Formula 55

The melting point of the obtained compound was 175.5° to 176.0° C.

EXAMPLE 22

The α-cyano-3,4-dimethoxy-3'-chlorostilbene (yellow crystal), 2.35 g (yield: 78.3%), were obtained according to the same procedure as in Example 2 except that 1.41 g (10.0 mmole) of 3-chlorobenzaldehyde (purchased from Tokyo Kasei) were used instead of 4-chlorobenzaldehyde.

The white crystalline compound, 436 mg (yield: 80.2%), represented by the following formula were obtained according to the same procedure as in Example 2 except that 600 mg (2.0 mmole) of the above α-cyano-3,4-dimethoxy-3'-chlorostilbene were used instead of α-cyano-3,4-dimethoxy-4'-chlorostilbene:

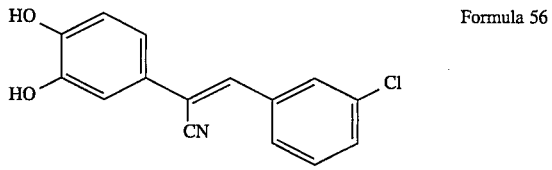

Formula 56

The melting point of the obtained compound was 189° to 190° C.

EXAMPLE 23

The α-cyano-3,4-dimethoxy-4'-bromostilbene (yellow crystal), 3.17 g (yield: 92.1%), were obtained according to the same procedure as in Example 2 except that 1.85 g (10.0 mmole) of 4-bromobenzaldehyde (purchased from Tokyo Kasei) were used instead of 4-chlorobenzaldehyde.

The white crystalline compound, 544 mg (yield: 86.0%), represented by the following formula were obtained according to the same procedure as in Example 2 except that 688 mg (2.0 mmole) of the above α-cyano-3,4-dimethoxy-4'-bromostilbene were used instead of α-cyano-3,4-dimethoxy-4-chlorostilbene:

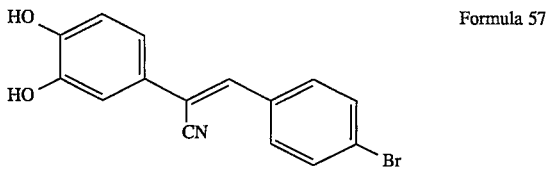

Formula 57

The melting point of the obtained compound was 171.0° to 171.5° C.

EXAMPLE 24

The α-cyano-3,4-dimethoxy-4'-methylstilbene (yellow crystal), 2.20 g (yield: 78.8%), were obtained according to the same procedure as in Example 2 except that 1.20 g (10.0 mmole) of 4-methylbenzaldehyde (purchased from Wako Junyaku Kogyo) were used instead of 4-chlorobenzaldehyde.

The white crystalline compound, 438 mg (yield: 87.1%), represented by the following formula were obtained according to the same procedure as in Example 2 except that 559 mg (2.0 mmole) of the above a -cyano-3,4-dimethoxy-4'-methylstilbene were used instead of α-cyano-3,4-dimethoxy-4'-chlorostilbene:

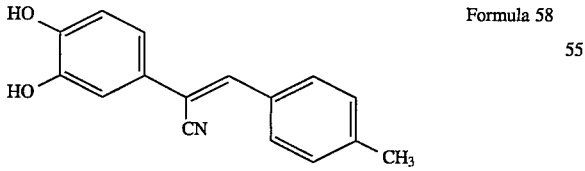

Formula 58

The melting point of the obtained compound was 162.5° to 163.0° C.

EXAMPLE 25

The a -cyano-3,4-dimethoxy-3'-methylstilbene (yellow crystal), 1.46 g (yield: 52.3%), were obtained according to the same procedure as in Example 2 except that 1.20 g (10.0 mmole) of 3-methylbenzaldehyde (purchased from Tokyo Kasei) were used instead of 4-chlorobenzaldehyde.

The yellow crystalline compound, 294 mg (yield: 58.5%), represented by the following formula were obtained according to the same procedure as in Example 2 except that 559 mg (2.0 mmole) of the above α-cyano-3,4-dimethoxy-3'-methylstilbene were used instead of α-cyano-3,4-dimethoxy-4'-chlorostilbene:

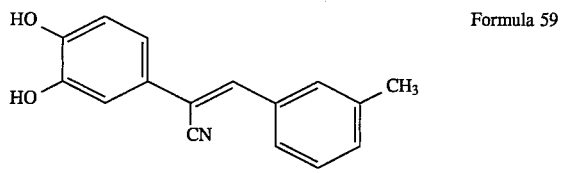

Formula 59

The melting point of the obtained compound was 110° to 111° C.

EXAMPLE 26

The α-cyano-3,4-dimethoxy-4'-ethylstilbene (light yellow crystal), 1.79 g (yield: 61.0%), were obtained according to the same procedure as in Example 2 except that 1.34 g (10.0 mmole) of 4-ethylbenzaldehyde (purchased from Tokyo Kasei) were used instead of 4-chlorobenzaldehyde.

The yellow crystalline compound, 448 mg (yield: 84.4%), represented by the following formula were obtained according to the same procedure as in Example 2 except that 587 mg (2.0 mmole) of the above α-cyano-3,4-dimethoxy-4'-ethylstilbene were used instead of α--cyano-3,4-dimethoxy-4'-chlorostilbene:

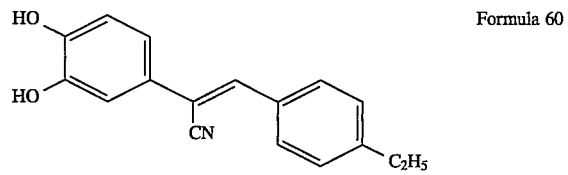

Formula 60

The melting point of the obtained compound was 140.5° to 141.0° C.

EXAMPLE 27

The α-(3,4-dimethoxyphenyl)-β-(5-methylthiophen-2-yl)acrylonitrile (light yellow crystal), 2.36 g (yield: 82.7%), were obtained according to the same procedure as in Example 2 except that 1.26 g (10.0 mmole) of 5-methylthiophene-2-carboxaldehyde (purchased from Tokyo Kasei) were used instead of 4-chlorobenzaldehyde.

The orange crystalline compound, 400 mg (yield: 77.7%), represented by the following formula were obtained according to the same procedure as in Example 2 except that 571 mg (2.0 mmole) of the above α-(3,4-dimethoxyphenyl)-β-(5-methylthiophen-2-yl)acrylonitrile were used instead of α-cyano-3,4-dimethoxy-4'-chlorostilbene:

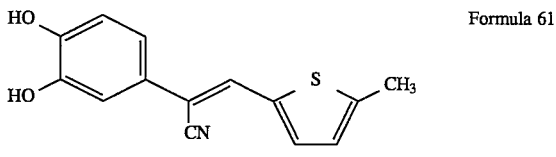

Formula 61

The melting point of the obtained compound was 183.0° to 183° C.

EXAMPLE 28

The α-(3,4-dimethoxyphenyl)-β-(5-methylfuran-2-yl)acrylonitrile (yellow crystal), 2.16 g (yield: 80.2%), were obtained according to the same procedure as in Example 2 except that 1.10 g (10.0 mmole) of 5-methylfuran-2-carboxaldehyde (purchased from Wako Junyaku Kogyo) were used instead of 4-chlorobenzaldehyde.

The orange crystalline compound, 320 mg (yield: 66.3%), represented by the following formula were obtained according to the same procedure as in Example 2 except that 539 mg (2.0 mmole) of the above α-(3,4-dimethoxyphenyl)-β-(5-methylfuran-2-yl)acrylonitrile were used instead of α-cyano-3,4-dimethoxy-4'-chlorostilbene:

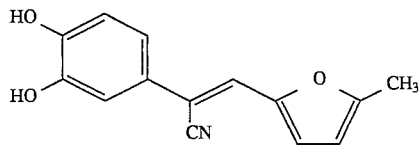

Formula 62

The melting point of the obtained compound was 150.5° to 151.0° C.

EXAMPLE 29

A mixture of 5-methylfuran-2-carboxaldehyde (5.51 g, 50 mmol, purchased from Wako Junyaku Kogyo), rhodanine (6.66 g, 50 mmol, purchased from Tokyo Kase), and anhydrous sodium acetate (2.3 g, 150 mmol, purchased from Kokusan Kagaku) in 35 ml of acetic acid (purchased from Wako Junyaku Kogyo) was refluxed for 30 minutes. After being cooled, the reaction mixture was poured into 500 ml of water. The precipitate was collected and washed with water, with ethanol, and then with ether to give 10.04 g (yield: 89.1%) of (5-methylfurylidene) rhodanine as an orange-brown color crystalline.

A suspension of the above compound in 65 ml of 15% sodium hydroxide solution was heated at 100° C. for 30 minutes. After being cooled, the reaction mixture was poured into 500 ml of 10% hydrochloric acid. The precipitate was collected and washed with water to give 8.22 g of 3-(5-methylfuryl)-2-thioketopropionic acid as a yellow crystalline.

To a mixture of 8.22 g of the above compound, 45 ml of ethanol, and hydroxylamine hydrochloride (10.1 g, 146 mmol, purchased from Wako Junyaku Kogyo) was added 55 ml of sodium ethoxide-21% denatured alcohol solution (147 mmol equivalent, purchased from Aldrich) gradually and heated at 100° C. After being cooled, the mixture was concentrated under reduced pressure. To the residue was added 20 ml of 5% sodium hydroxide solution and then was added 20 ml of 10% hydrochloric acid carefully under ice-cooling. The mixture was extracted with ether three times and the combined organic layer was washed with brine, and dried over anhydrous sodium sulfate. The solvent was removed. The residue was dissolved in a small amount of ether and then toluene was added to the solution till the mixture became slightly cloudy and the mixture was allowed to stand. The precipitate was collected and washed with toluene to give 4.55 g (yield: 53.3%) of 3-(5-methyl-2-furyl)-2-hydroxyiminopropionic acid as a yellow crystalline.

To a solution of 4.55 g of the above compound in 60 ml of benzene was added 1,1'-carbonyldiimidazole (3.97 g, 24.8 mmol, purchased from Aldrich) gradually and the mixture was heated at 70° C. for 1 hour. After being cooled, the mixture was poured into 50 ml of ice-water, and extracted with benzene three times. The combined organic layer was washed with aqueous sodium bicarbonate, with brine, with 1% hydrochloric acid, and then with water in order and dried over anhydrous sodium sulfate. The solvent was removed under reduced pressure. The residual oil (2.4 g) was purified on silica gel chromatography (ethyl acetate: hexane=1:4) to give 2.00 g (yield: 66.6%) of 5-methylfuran-2-ylacetonitrile as a colorless oil.

5-methyl-α-(3,4-dimethoxybenzylidene)furan-2-acetonitrile (yellow crystal), 419 mg (yield: 31.1%), were obtained according to the same procedure as in Example 2 except that 606 mg (5.0 mmole) of the above 5-methylfuran-2-ylacetonitrile and 831 mg (5.0 mmole) of 3,4-dimethoxybenzaldehyde (purchased from Tokyo Kasei) were used.

The orange crystalline compound, 140 mg (yield: 48.4%), represented by the following formula were obtained according to the same procedure as in Example 2 except that 323 mg (1.2 mmole) of the above 5-methyl-α-(3,4-dimethoxybenzylidene)furan-2-acetonitrile and 1.73 g (15 mmole) of pyridinium chloride (purchased from Wako Junyaku Kogyo) were used instead of α-cyano-3,4-dimethoxy-4'-chlorostilbene:

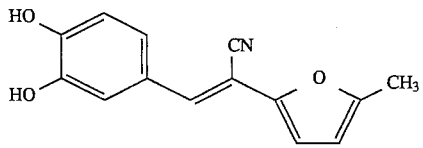

Formula 63

The melting point of the obtained compound was 153.0° to 153.5° C.

The measured values of the nuclear magnetic resonance spectra and infrared absorption spectra of the compounds and intermediates of the third embodiment according to the present invention prepared in the following Referential Examples and Examples are shown in Tables 14–22, The nuclear magnetic resonance spectra [$^1$NMR (500 MHz)] were measured in a DMSO-$d_6$ solution with tetramethylsilane as internal standard or in a mixed solution of CDCl$_3$ with a few drops of CD$_3$OD added therein; and the infrared absorption spectra were measured according to a KBr tablet method,

TABLE 14

| Compound | Structural formula | $^1$H-NMR (DMSO-$d_6$, δppm) | IR (vcm$^{-1}$) |
|---|---|---|---|
| Formula 34b | CH$_3$COO— ... —CN ... —Cl (CH$_3$COO) | 2.32(3H, s), 2.33(3H, s), 7.48(1H, d), 7.61 (2H, d), 7.79(2H, d), 7.82 (1H, d), 7.88(1H, dd), 8.10(1H, s) | 2220, 1775, 1505, 1375, 1265, 1215, 1190, 1110, 1010, 830 |

TABLE 14-continued

| Compound | Structural formula | $^1$H-NMR (DMSO-$d_6$, δppm) | IR (vcm$^{-1}$) |
|---|---|---|---|
| Formula 35b | CH$_3$CH$_2$COO-, CH$_3$CH$_2$COO- substituted benzene –CH=C(CN)– C$_6$H$_4$–Cl | 1.14(3H, t), 1.15(3H, t), 2.63(2H, q), 2.64(2H, q), 7.48(1H, d), 7.60 (2H, d), 7.79(2H, d), 7.82(1H, d), 7.89(1H, dd), 8.09(1H, s) | 3000, 2950, 2220, 1775, 1760, 1505, 1495, 1460, 1420, 1360, 1295, 1265, 1205, 1140, 1120, 1070, 1010, 980, 840 |
| Formula 36b | CH$_3$(CH$_2$)$_2$COO-, CH$_3$(CH$_2$)$_2$COO- substituted benzene –CH=C(CN)– C$_6$H$_4$–Cl | 0.977(3H, t), 0.982(3H, t), 1.659 (2H, hex), 1.665(2H, hex), 2.586 (2H, t), 2.600(2H, t), 7.48(1H, d), 7.60(2H, d), 7.79(2H, d), 7.81(1H, d), 7.90(1H, dd), 8.10(1H, s) | 2980, 2950, 2890, 2220, 1770, 1515, 1500, 1465, 1425, 1365, 1265, 1250, 1155, 1135, 1095, 960, 830 |
| Formula 37b | CH$_3$(CH$_2$)$_4$COO-, CH$_3$(CH$_2$)$_4$COO- substituted benzene –CH=C(CN)– C$_6$H$_4$–Cl | 0.89(6H, m), 1.34(8H, m), 1.64 (4H, m), 2.60(2H, t), 2.61(2H, t), 7.47(1H, d), 7.60(2H, d), 7.79(2H, d), 7.81(1H, d), 7.89(1H, dd), 8.10(1H, s) | 2980, 2950, 2890, 2880, 2225, 1775, 1520, 1500, 1475, 1430, 1375, 1275, 1270, 1250, 1240, 1215, 1140, 1100, 990, 980, 960, 830 |
| Formula 39b | CH$_3$COO-, CH$_3$COO- substituted benzene –C(CN)=CH– C$_6$H$_4$–Cl | 2.31(3H, s), 2.32(3H, s), 7.45(1H, d), 7.64(2H, d), 7.68–7.72(2H, m), 7.95(2H, d), 8.09(1H, s) | 2220, 1785, 1765, 1590, 1505, 1430, 1370, 1265, 1200, 1125, 1010 |

TABLE 15

| Compound | Structural formula | $^1$H-NMR (DMSO-$d_6$, δppm) | IR (vcm$^{-1}$) |
|---|---|---|---|
| Formula 40b | CH$_3$COO-, CH$_3$COO- substituted benzene –C(CN)=CH– C$_6$H$_4$–Cl (meta) | 2.31(3H, s), 2.32(3H, s), 7.46(1H, d), 7.59(2H, m), 7.68–7.72(2H, m), 7.90(1H, m), 7.97(1H, m), 8.09(1H, s) | 2230, 1780, 1770, 1610, 1565, 1520, 1440, 1420, 1380, 1360, 1310, 1280, 1270, 1220, 1200, 1170, 1130, 1030, 1015, 910, 795, 690 |
| Formula 42b | CH$_3$COO-, CH$_3$COO- substituted benzene –C(CN)=CH– C$_6$H$_4$–F | 2.31(3H, s), 2.32(3H, s), 7.42(2H, t), 7.44(1H, d), 7.67–7.71(2H, m), 8.01(1H, dd), 8.09(1H, s) | 2210, 1770, 1600, 1510, 1376, 1270, 1230, 1210, 1195, 1170, 1130 |
| Formula 44b | CH$_3$COO-, CH$_3$COO- substituted benzene –C(CN)=CH– C$_6$H$_4$–Br | 2.30(3H, s), 2.32(3H, s), 7.44(1H, d), 7.68–7.72(2H, m), 7.77(2H, d), 7.87(2H, d), 8.07(1H, s) | 2220, 1780, 1760, 1580, 1500, 1430, 1370, 1260, 1200, 1165, 1125, 1075, 1005 |

TABLE 15-continued

| Compound | Structural formula | $^1$H-NMR (DMSO-$d_6$, δppm) | IR (vcm$^{-1}$) |
|---|---|---|---|
| Formula 46b | (CH$_3$COO)$_2$-phenyl-CH=C(CN)-phenyl-I | 2.31(3H, s), 2.33(3H, s), 7.47(1H, d), 7.56(2H, d), 7.81(1H, d), 7.88 (1H, dd), 7.90(2H, d), 8.10(1H, s) | 2220, 1770, 1505, 1435, 1370, 1265, 1240, 1215, 1120 |
| Formula 48b | (CH$_3$COO)$_2$-phenyl-C(CN)=CH-phenyl-CH$_3$ | 2.30(3H, s), 2.32(3H, s), 2.38(3H, s), 7.37(2H, d), 7.42(1H, d), 7.66–7.70(2H, m), 7.85(2H, d), 8.03(1H, s) | 3075, 2230, 1780, 1605, 1520, 1510, 1435, 1375, 1295, 1285, 1270, 1220, 1200, 1170, 1120, 1110, 1020, 900, 810 |

TABLE 16

| Compound | Structural formula | $^1$H-NMR (DMSO-$d_6$, δppm) | IR (vcm$^{-1}$) |
|---|---|---|---|
| Formula 50b | (CH$_3$COO)$_2$-phenyl-C(CN)=CH-phenyl-CH$_3$ (meta) | 2.31(3H, s), 2.32(3H, s), 2.38(3H, s), 7.34(1H, d), 7.43(1H, d), 7.44 (1H, I), 7.67–7.71(2H, m), 7.74 (1H, s), 7.76(1H, d), 8.04(1H, s) | 3060, 2960, 2230, 1780, 1770, 1615, 1600, 1520, 1420, 1370, 1305, 1275, 1220, 1200, 1180, 1170, 1130, 1015, 895, 855, 795, 695 |
| Formula 52b | (CH$_3$COO)$_2$-phenyl-C(CN)=CH-phenyl-C$_2$H$_5$ | 1.22(3H, I), 2.30(3H, s), 2.32(3H, s), 2.68(2H, q), 7.40(2H, d), 7.43 (1H, d), 7.68–7.70(2H, m), 7.87 (2H, d), 8.04(1H, s) | 2975, 2940, 2220, 1770, 1605, 1570, 1425, 1370, 1270, 1210, 1190, 1160, 1120 |
| Formula 54b | (CH$_3$COO)$_2$-phenyl-CH=C(CN)-phenyl-CF$_3$ | 2.32(3H, s), 2.34(3H, s), 7.50(1H, d), 7.86(1H, d), 7.90(2H, d), 7.92 (1H, dd), 7.99(2H, d), 8.23(1H, s) | 2230, 1780, 1605, 1510, 1440, 1425, 1380, 1340, 1275, 1240, 1220, 1195, 1130, 1080, 1020, 920, 850 |
| Formula 56b | (CH$_3$COO)$_2$-phenyl-CH=C(CN)-phenyl-OCH$_3$ | 2.31(3H, s), 2.33(3H, s), 3.82(3H, s), 7.09(2H, d), 7.45(1H, d), 7.70 (2H, d), 7.77(1H, d), 7.85(1H, dd), 7.92(1H, s) | 2230, 1790, 1780, 1620, 1520, 1375, 1290, 1275, 1220, 1190, 1120, 1035, 1020, 840 |
| Formula 58b | (CH$_3$COO)$_2$-phenyl-C(CN)=CH-phenyl | 2.31(3H, s), 2.32(3H, s), 7.44(1H, d), 7.50–7.58(3H, m), 7.68–7.72 (2H, m), 7.94(2H, d), 8.09(1H, s) | 2225, 1775, 1760, 1510, 1365, 1265, 1230, 1220, 1195, 1170, 1120, 900, 690 |

TABLE 17

| Compound | Structural formula | ¹H-NMR (DMSO-d₆, δppm) | IR (vcm⁻¹) |
|---|---|---|---|
| Formula 60b | CH₃COO-, CH₃COO- substituted phenyl-CH=C(CN)-C₆H₄-NO₂ | 2.33(3H, s), 2.34(3H, s), 7.52(1H, d), 7.88(1H, d), 7.95(1H, dd), 8.05 (2H, dd), 8.31(1H, s), 8.37(2H, d) | 2220, 1780, 1765, 1590, 1520, 1370, 1350, 1265, 1200, 1120, 1010, 855, 755 |
| Formula 62B | CH₃COO-, CH₃COO- substituted phenyl-C(CN)=CH-thiophene (2-yl) | 2.30(3H, s), 2.32(3H, s), 7.28(1H, dd), 7.42(1H, d), 7.63–7.67(2H, m), 7.77(1H, d), 7.95(1H, d), 8.33 (1H, s) | 3140, 2230, 1780, 1770, 1600, 1515, 1440, 1420, 1375, 1340, 1280, 1240, 1230, 1200, 1180, 1130, 1020, 900, 880, 725, 720 |
| Formula 64b | CH₃COO-, CH₃COO- substituted phenyl-C(CN)=CH-thiophene (3-yl) | 2.30(3H, s), 2.32(3H, s), 7.42(1H, d), 7.63–7.66(2H, m), 7.77(1H, dd), 7.79(1H, dd), 8.10(1H, s), 8.22(1H, m) | 3130, 2960, 2230, 1780, 1770, 1610, 1520, 1435, 1380, 1350, 1310, 1280, 1235, 1200, 1180, 1130, 1020, 900, 860, 790 |
| Formula 66b | CH₃COO-, CH₃COO- substituted phenyl-CH=C(CN)-(4-Br-thiophene) | 2.31(3H, s), 2.33(3H, s), 7.47(1H, d), 7.51(1H, d), 7.78(1H, d), 7.85 (1H, d), 7.86(1H, dd), 7.95(1H, s) | 3120, 2240, 1780, 1515, 1430, 1375, 1335, 1260, 1220, 1190, 1120, 1025, 830 |
| Formula 68b | CH₃COO-, CH₃COO- substituted phenyl-C(CN)=CH-(5-CH₃-thiophene) | 2.29(3H, s), 2.31(3H, s), 2.56(3H, s), 6.99(1H, d), 7.40(1H, d), 7.57 (1H, d), 7.60–7.63(2H, m), 8.22(1H, s) | 3070, 2230, 1780, 1600, 1515, 1465, 1440, 1380, 1280, 1220, 1200, 1180, 1125, 1115, 1025, 810 |

TABLE 18

| Compound | Structural formula | ¹H-NMR (DMSO-d₆, δppm) | IR (vcm⁻¹) |
|---|---|---|---|
| Formula 70b | CH₃COO-, CH₃COO- substituted phenyl-C(CN)=CH-(5-CH₃-furan) | 2.29(3H, s), 2.31(3H, s), 2.41(3H, s), 6.43(1H, d), 7.07(H, d), 7.38 (1H, d), 7.61(2H, m), 7.82(1H, s) | 3130, 3060, 2220, 1780, 1600, 1590, 1510, 1380, 1340, 1275, 1225, 1210, 1190, 1160, 1130, 1110, 1040, 1015, 895, 800 |
| Formula 72b | CH₃COO-, CH₃COO-, CH₃COO- substituted phenyl-CH=C(CN)-C₆H₄-Cl | 2.33(6H, s), 2.34(3H, s), 7.61(2H, d), 7.76(2H, s), 7.79(2H, d), 8.09 (1H, s) | 2225, 1780, 1500, 1440, 1375, 1325, 1310, 1220, 1195, 1140, 1060, 1010, 830 |

TABLE 19

| Compound | Structural formula | $^1$H-NMR (CDCl$_3$ + CD$_3$OD, δppm) | IR (vcm$^{-1}$) |
|---|---|---|---|
| Formula 32b | HO-/HO- phenyl -CH=C(CN)- phenyl-Cl | 6.91(1H, d), 7.17(1H, dd), 7.39 (1H, s), 7.40(2H, d), 7.55(2H, d), 7.64(1H, d) | 3300, 2220, 1600, 1585, 1515, 1495, 1450, 1410, 1360, 1310, 1300, 1245, 1160, 1110, 1090, 1010, 950, 910, 830, 820, 800, 740, 715 |
| Formula 38b | HO-/HO- phenyl -C(CN)=CH- phenyl-Cl | 6.89(1H, d), 7.09(1H, dd), 7.15 (1H, d), 7.36(1H, s), 7.42(2H, d), 7.77(2H, d) | 3500, 3300, 2230, 1610, 1590, 1530, 1490, 1440, 1380, 1365, 1310, 1300, 1285, 1270, 1225, 1200, 1170, 1120, 1100, 1010, 860, 790 |
| Formula 33b | HO-/HO- phenyl -C(CN)=CH- phenyl-Cl (3-Cl) | 6.89(1H, d), 7.09(1H, dd), 7.15 (1H, d), 7.35(1H, s), 7.36–7.42 (2H, m), 7.75(2H, m) | 3400, 3280, 2240, 1610, 1590, 1580, 1540, 1485, 1445, 1340, 1310, 1300, 1280, 1225, 1200, 1185, 1120, 870, 810, 790, 700, 680 |
| Formula 41b | HO-/HO- phenyl -C(CN)=CH- phenyl-F | 6.89(1H, d), 7.08(1H, dd), 7.14 (2H, l), 7.14(1H, d), 7.37(1H, s), 7.83(2H, dd) | 3370, 2230, 1610, 1520, 1445, 1385, 1300, 1255, 1175, 1130, 1115, 1020, 915, 860, 825, 805, 790 |
| Formula 43b | HO-/HO- phenyl -C(CN)=CH- phenyl-Br | 6.89(1H, d), 7.09(1H, dd), 7.15 (1H, d), 7.33(1H, s), 7.58(2H, d), 7.70(2H, d) | 3550, 3300, 2245, 1610, 1590, 1530, 1490, 1440, 1410, 1385, 1370, 1300, 1240, 1210, 1200, 1180, 1135, 1080, 1010, 910, 865, 810, 785, 770 |

TABLE 20

| Compound | Structural formula | ¹H-NMR (CDCl₃ + CD₃OD, δppm) | IR (vcm⁻¹) |
|---|---|---|---|
| Formula 45b | HO-[3,4-dihydroxyphenyl]-CH=C(CN)-[4-iodophenyl] | 6.90(1H, d), 7.19(1H, dd), 7.36 (2H, d), 7.41(1H, s), 7.62(1H, d), 7.75(2H, d) | 3370, 3220, 2230, 1585, 1520, 1485, 1450, 1400, 1375, 1290, 1245, 1195, 1120, 1065, 1000, 955, 820, 805 |
| Formula 47b | HO-[3,4-dihydroxyphenyl]-C(CN)=CH-[4-methylphenyl] | 2.40(3H, s), 6.89(1H, d), 7.08(1H, dd), 7.14(1H, d), 7.25(1H, d), 7.38 (1H, s), 7.74(2H, d) | 3550, 3300, 2240, 1615, 1530, 1460, 1400, 1360, 1300, 1270, 1216, 1195, 1135, 910, 860, 815, 795, 790, 770, 755, 710 |
| Formula 49b | HO-[3,4-dihydroxyphenyl]-C(CN)=CH-[3-methylphenyl] | 2.38(3H, s), 6.86(1H, d), 7.06(1H, dd), 7.13(1H, d), 7.20(1H, d), 7.32 (1H, t), 7.37(1H, s), 7.60(1H, s), 7.63(1H, d) | 3470, 3300, 2230, 1625, 1610, 1600, 1580, 1530, 1520, 1476, 1440, 1360, 1295, 1275, 1250, 1220, 1200, 1125, 1110, 850, 810, 790, 775, 740, 680 |
| Formula 51b | HO-[3,4-dihydroxyphenyl]-C(CN)=CH-[4-ethylphenyl] | 1.26(3H, t), 2.70(2H, q), 6.89(1H, d), 7.09(1H, dd), 7.15(1H, d), 7.28(2H, d), 7.39(1H, s), 7.76(2H, d) | 3470, 3180, 2990, 2950, 2260, 1620, 1520, 1475, 1400, 1370, 1340, 1300, 1230, 1215, 1115, 1065, 1030, 930, 905, 885, 835, 815, 795, 695 |
| Formula 53b | HO-[3,4-dihydroxyphenyl]-CH=C(CN)-[4-trifluoromethylphenyl] | 6.93(1H, d), 7.20(1H, dd), 7.49 (1H, s), 7.68(2H, d), 7.69(1H, d), 7.74(2H, d) | 3330, 2225, 1620, 1600, 1586, 1515, 1425, 1360, 1330, 1300, 1250, 1170, 1135, 1120, 1070, 1010, 960, 920, 875, 870, 850, 810, 740 |

TABLE 21

| Compound | Structural formula | ¹H-NMR (CDCl₃ + CD₃OD, δppm) | IR (vcm⁻¹) |
|---|---|---|---|
| Formula 55b | HO-[3,4-dihydroxyphenyl]-CH=C(CN)-[4-methoxyphenyl] | 3.85(3H, s), 6.89(1H, d), 6.95(2H, d), 7.16(1H, dd), 7.31(1H, s), 7.55 (2H, d), 7.58(1H, d) | 3425, 3350, 2220, 1610, 1600, 1525, 1510, 1450, 1380, 1300, 1280, 1255, 1205, 1180, 1125, 1110, 1035, 1020, 865, 830 |
| Formula 57b | HO-[3,4-dihydroxyphenyl]-C(CN)=CH-phenyl | 6.90(1H, d), 7.10(1H, dd), 7.16 (1H, d), 7.41(1H, t), 7.42(1H, s), 7.45(2H, t), 7.83(2H, d) | 3550, 3460, 3300, 2240, 1605, 1520, 1450, 1440, 1370, 1300, 1216, 1200, 1180, 1120, 870, 855, 790, 770, 745, 690 |
| Formula 59b | HO-[3,4-dihydroxyphenyl]-CH=C(CN)-[4-nitrophenyl] · ¼ H₂O | 6.93(1H, d), 7.28(1H, dd), 7.58 (1H, s), 7.67(1H, d), 7.80(2H, d), 8.29(2H, d) | 3520, 3430, 2225, 1595, 1580, 1520, 1355, 1345, 1310, 1300, 1210, 1175, 1130, 860, 850, 765, 690 |

TABLE 21-continued

| Compound | Structural formula | $^1$H-NMR (CDCl$_3$ + CD$_3$OD, δppm) | IR (vcm$^{-1}$) |
|---|---|---|---|
| Formula 61b | HO, HO-phenyl-C(CN)=CH-thiophene | 6.88(1H, d), 7.07(1H, dd), 7.12 (1H, d), 7.13(1H, dd), 7.50(1H, d), 7.53(1H, s), 7.60(1H, d) | 3500, 3300, 3120, 2250, 1620, 1540, 1450, 1400, 1375, 1360, 1335, 1320, 1295, 1240, 1205, 1175, 1120, 1060, 865, 730 |
| Formula 63b | HO, HO-phenyl-C(CN)=CH-thiophene (3-isomer) | 6.88(1H, d), 7.07(1H, dd), 7.13 (1H, d), 7.40(1H, dd), 7.41(1H, s), 7.72(1H, d), 7.87(1H, d) | 3500, 3300, 2250, 1620, 1540, 1450, 1390, 1370, 1330, 1315, 1285, 1255, 1220, 1210, 1190, 1160, 1125, 870, 780 |

TABLE 22

| Compound | Structural formula | $^1$H-NMR (CDCl$_3$ + CD$_3$OD, δppm) | IR (vcm$^{-1}$) |
|---|---|---|---|
| Formula 65b | HO, HO-phenyl-CH=C(CN)-thiophene-Br | 6.90(1H, d), 7.15(1H, dd), 7.17 (1H, d), 7.20(1H, d), 7.25(1H, s), 7.57(1H, d) | 3510, 3330, 3120, 2230, 1615, 1595, 1580, 1520, 1510, 1450, 1430, 1370, 1330, 1290, 1270, 1200, 1165, 1120, 985, 900, 860, 820, 740 |
| Formula 67b | HO, HO-phenyl-C(CN)=CH-thiophene-CH$_3$ | 2.55(3H, s), 6.78(1H, d), 6.86(1H, d), 7.03(1H, dd), 7.09(1H, d), 7.34 (1H, d), 7.44(1H, s) | 3540, 3300, 2225, 1620, 1605, 1590, 1530, 1520, 1455, 1385, 1360, 1315, 1290, 1240, 1215, 1200, 1180, 1130, 1120, 1060, 1020, 875, 810, 790, 745 |
| Formula 69b | HO, HO-phenyl-C(CN)=CH-furan-CH$_3$ | 2.39(3H, s), 6.17(1H, d), 6.87(1H,d), 6.98(1H, d), 7.03(1H, dd), 7.09 (1H, d), 7.16(1H, s) | 3480, 3280, 3240, 2230, 1625, 1610, 1515, 1445, 1390, 1370, 1355, 1310, 1295, 1280, 1245, 1225, 1205, 1185, 1130, 1115, 1035, 865, 860, 790, 740 |
| Formula 71b | HO, HO, HO-phenyl-CH=C(CN)-phenyl-Cl | 7.05(2H, s), 7.32(1H, s), 7.40(2H, d), 7.54(2H, d) | 3425, 2230, 1620, 1600, 1540, 1500, 1455, 1420, 1350, 1210, 1160, 1105, 1040, 825 |

Referential Example 1

[Preparation of α-Cyano-4-Chloro-3',4'-Dihydroxystilbene]

To a mixture of 758 mg (5.00 mmole) of 4-chlorophenylacetonitrile (purchased from Tokyo Kasei), 691 mg (5.00 mmole) of 3,4-dihydroxybenzaldehyde (purchased from Tokyo Kasei) and 10 ml of ethanol (purchased from Kokusan Kagaku) were added 0.54 ml of piperidine (purchased from Wako Junyaku Kogyo), the mixture was refluxed with heating for 6 hours and air-cooled, the reaction product was added to 100 ml of 1N hydrochloric acid, and deposits were filtered, washed with water, dissolved in ethyl acetate, washed with a 20% sodium hydrogensulfite solution twice and subsequently with saturated saline once and dried over sodium anhydrous sulfate. Then, the solvent was distilled off under reduced pressure, and the residue was purified according to silica gel column chromatography (effluent with a ratio of hexane to ethyl acetate of 5:1 to 5:2 used) to obtain 919 mg (yield: 67.6%) of α-cyano-4-chloro-3',4'-dihydroxystilbene (yellow crystal) represented by the following formula:

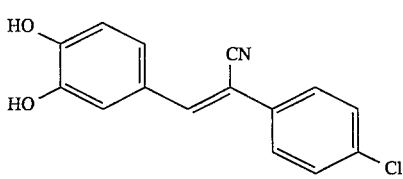

Formula 32b

Referential Example 2

[Preparation of α-Cyano-3'-Chloro-3,4-Dimethoxystylbene]

3,4-dimethoxyphenylacetonitrile (purchased from Tokyo Kasei), 1.77 g (10.0 mmole), and 1.41 g (10.0 mmole) of 3-chlorobenzaldehyde (purchased from Tokyo Kasei) were dissolved with heating into 10 ml of ethanol (purchased from Kokusan Kagaku), two drops of a 20% sodium hydroxide solution were added thereto, the mixture was stirred overnight, and deposited crystals were filtered, washed with ethanol twice and subsequently with hexane twice and dried to obtain 2.35 g (yield: 78.3%) of α-cyano-3'-chloro-3,4-dimethoxystilbene (yellow crystal).

Referential Example 3

[Preparation of α-Cyano-3'-Chloro-3,4-Hydroxystylbene]

A mixture of 600 mg (2.00 mmole) of α-cyano-3'-chloro-3,4-dimethoxyetilbene obtained according to the same procedure as in Referential Example 2 and 3.5 g (30 mmole) of pyridinium chloride (purchased from Wako Junyaku Kogyo) was melted and mixed on an oil bath heated to 210° C. in advance in an atmosphere of argon gas, stirred at the same temperature for one hour and air-cooled, 20 ml of 2N hydrochloric acid were added to the consolidated reaction product, the mixture was disintegrated and stirred for 30 minutes, and then deposits were filtered, washed with water three times, dried and purified by means of a silica gel short column (ethyl acetate used as an effluent) to obtain 436 mg (yield: 80.2%) of α-cyano-3'-chloro-3,4-dihydroxystilbene (yellow crystal):

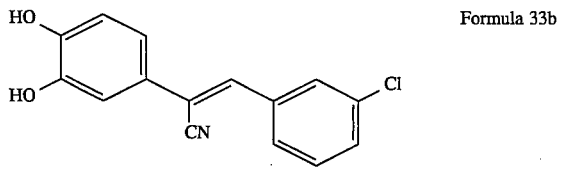

Formula 33b

Referential Example 4

[Preparation of 4-Iodophenylacetonitrile]

A mixture of p-iodotoluene (4.36 g, 20 mmol, purchased from Tokyo Kasei) and N-bromosuccinimide (3.92 g, 22 mmol, purchased from Tokyo Kasei) in 60 ml of carbontetrachloride (purchased from Wako Junyaku Kogyo) was refluxed for 4 hours under irradiation by means of an incandescent lamp to give 2.67 g (yield: 45.0%) of 4-iodobenzyl bromide as a white crystalline.

To a hot solution (50° C.) of sodium cyanide 0.49 g, 10.0 mmom, purchased from Kokusan Kagaku) in 10 ml of dimethyl sulfoxide (purchased from Aldrich) was added the above 4-iodobenzyl bromide (1.48 g, 5.0 mmol) and the mixture was stirred for three hours at ambient temperature. To the resultant reaction mass was added water and extracted with hexane. The solvent was removed to give 0.84 g (yield: 69%) of 4-iodophenylacetonitrile as a white crystalline.

Referential Example 5

[Preparation of 4-Bromothiophene-2-Ylacetonitrile]

To a solution of 4-bromothiophene-2-carboxaldehyde (9.55 g, 50 mmol, purchased from Aldrich) in 100 ml of ethanol was added sodium borohydride (3.78 g, 100 mmol purchased from Yoneyama Yakuhin) gradually under cooling in an ice bath. After the completion of addition, the mixture was stirred further for 1.5 hours at room temperature. The reaction mixture was acidified with hydrochlorid acid, then was concentrated to dryness under reduced pressure. To the residue was added water and extracted with ether to give 9.29 g (yield: 96%) of 4-bromothiophen-2-ylmethanol as an oil.

A mixture of the above 4-bromothiophen-2-ylmethanol (4.83 g, 25 mmol) and 63 ml of 47% hydrobromic acid was stirred vigorously for 30 minutes at room temperature. The reaction mixture was extracted with pentane to give 5.31 g (yield: 82.8%) of 2-bromomethyl-4-bromothiophene as a pale yellow oil. Thus obtained 5.12 g of 2-bromomethyl-4-bromothiophene was reacted with sodium cyanide according to the same procedure as in the synthesis of 4-iodophenylacetonitrile of example 5 to give 1.50 g (yield: 37.0%)of 4-bromothiophen-2-ylacetonitrile as a white crystal, removing by-product of α,α-bis[(4-bromothiophen-2-yl)methyl]-4-bromothiopheneaetonitrile by means of recrystalization.

EXAMPLE 30

The α-cyano-4-chloro-3',4'-dihydroxystilbene, 136 mg (0.50 mmole), obtained according to the same procedure as in Referential Example 1 were suspended in 1 ml of acetic anhydride (purchased from Wako Junyaku Kogyo), 0.5 ml of triethylamine (purchased from Kokusan Kagaku) were added thereto under ice cooling and stirred, then stirred at room temperature overnight, the obtained reaction product was added to 15 ml of 1N hydrochloric acid and stirred for 30 minutes, and deposited crystals were filtered, washed with water, dried and recrystallized from ethyl acetate-hexane to obtain 147 mg (yield: 82.6%) of a white crystalline compound represented by the following formula:

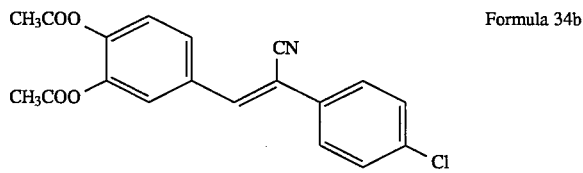

Formula 34b

The melting point of the obtained compound was 119.5° to 120° C.

EXAMPLE 31

The α-cyano-4-chloro-3',4'-dihydroxystilbene, 543 mg (2.00 mmole), obtained according to the same procedure as in Referential Example 1 were suspended in 10 ml of methylene chloride (purchased from Kokusan Kagaku), 0.69 ml of triethylamine (purchased from Kokusan Kagaku) were added thereto and stirred, the obtained orange transparent solution was ice-cooled, 0.44 ml of propionyl chloride (purchased from Tokyo Kasei) were dropped therein and stirred under ice cooling, then stirred at room temperature for one hour, ethyl acetate was added to the obtained reaction product, the resultant product was washed with 1N hydrochloric acid, a sodium hydrogencarbonate solution and saturated saline in order and dried over sodium anhydrous surface, the solvent was distilled off under reduced pressure, and the residue was recrystallized from ethyl acetate-hexane to obtain 664 mg (yield: 86.5%) of a white crystalline compound represented by the following formula:

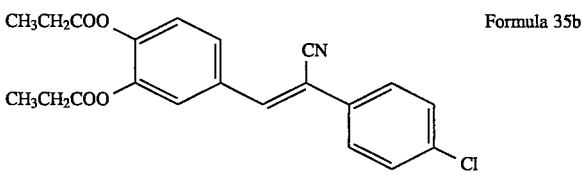

Formula 35b

The melting point of the obtained compound was 107.0° to 107.5° C.

EXAMPLE 32

The white crystalline compound, 740 mg (yield: 89.8%), represented by the following formula were obtained according to the same procedure as in Example 31 except that 0.52 ml of butyryl chloride (purchased from Tokyo Kasei) were used instead of propionyl chloride:

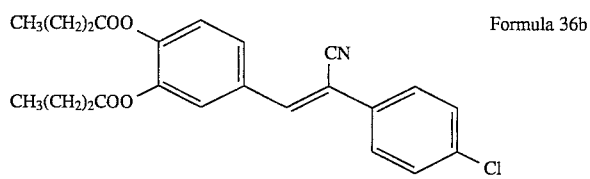

Formula 36b

The melting point of the obtained compound was 86.0° to 86.5° C.

EXAMPLE 33

The white crystalline compound, 428 mg (yield: 45.7%), represented by the following formula were obtained according to the same procedure as in Example 31 except that 0.69 ml of hexanoyl chloride (purchased from Tokyo Kasei) were used instead of propionyl chloride:

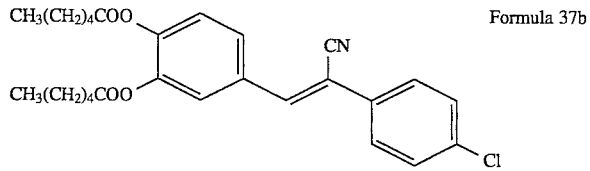

Formula 37b

The melting point of the obtained compound was 61.5° to 62.0° C.

EXAMPLE 34

The α-cyano-4'-chloro-3,4-dimethoxystilbene, 2.39 g (yield: 79.7%), were obtained according to the same procedure as in Referential Example 2 except that 1.41 g (10 mmole) of 4-chlorobenzaldehyde (purchased from Tokyo Kasei) were used instead of 3-chlorobenzaldehyde.

The α-cyano-4'-chloro-3,4-dihydroxystilbene, 455 mg (yield: 67.0%), represented by the following formula were obtained according to the same procedure as in Referential Example 3 except that 749 mg (2.50 mmole) of the above α-cyano-4'-chloro-3,4-dimethoxystilbene were used instead of α-cyano-3'-chloro-3,4-dimethoxystilbene and that 2.3 g (20 mmol) of pyridinium chloride (purchased from Wako Junyaku Kogyo) were used:

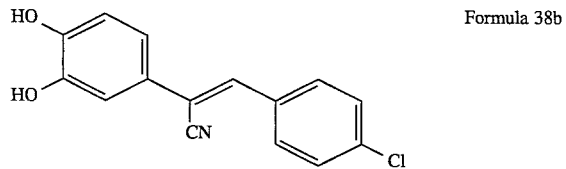

Formula 38b

The white crystalline compound, 153 mg (yield: 86.0%), represented by the following formula were obtained according to the same procedure as in Example 30 except that 136 mg (0.50 mmole) of the above α-cyano-4'-chloro-3,4-dihydroxystilbene were used instead of α-cyano-4-chloro-3',4'-dihydroxystilbene:

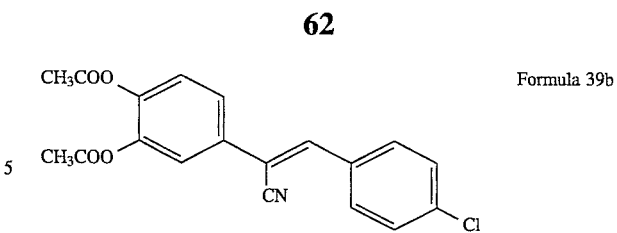

Formula 39b

The melting point of the obtained compound was 130.0° to 130.5° C.

EXAMPLE 35

The white crystalline compound, 109 mg (yield: 61.5%), represented by the following formula were obtained according to the same procedure as in Example 30 except that 136 mg (0.50 mmole) of α-cyano-3'-chloro-3,4-dihydroxystilbene obtained according to the same procedure as in Referential Example 3 were used instead of α-cyano-4-chloro-3',4'-dihydroxystilbene:

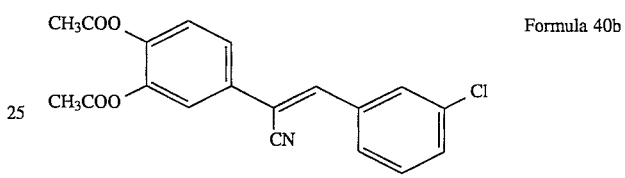

Formula 40b

The melting point of the obtained compound was 114.0° to 114.5° C.

EXAMPLE 36

The α-cyano-4'-fluoro-3,4-dimethoxystilbene, 2.33 g (yield: 82.2%), were obtained according to the same procedure as in Referential Example 2 except that 1.24 g (10 mmole) of 4-fluorobenzaldehyde (purchased from Tokyo Kasei) were used instead of 3-chlorobenzaldehyde.

The α-cyano-4'-fluoro-3,4-dihydroxystilbene, 432 mg (yield: 84.6%), represented by the following formula were obtained according to the same procedure as in Referential Example 3 except that 567 mg (2.00 mmole) of the above α-cyano-4'-fluoro-3,4-dimethoxystilbene were used instead of α-cyano-3'-chloro-3,4-dimethoxystilbene:

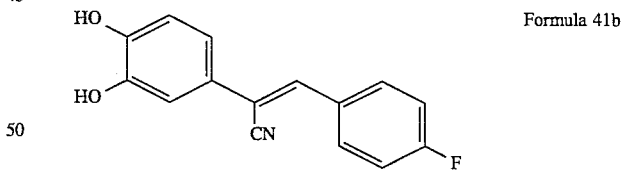

Formula 41b

The white crystalline compound, 151 mg (yield: 88.8%), represented by the following formula were obtained according to the same procedure as in Example 30 except that 128 mg (0.50 mmole) of the above α-cyano-4'-fluoro-3,4-dihydroxystilbene were used instead of α-cyano-4-chloro-3',4'-dihydroxystilbene:

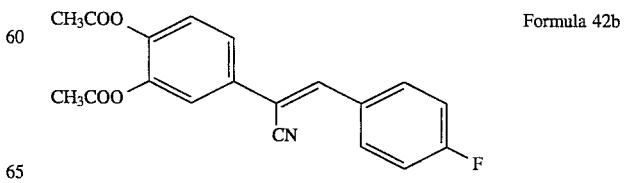

Formula 42b

The melting point of the obtained compound was 145.5° to 146.0° C.

EXAMPLE 37

The α-cyano-4'-bromo-3,4-dimethoxystilbene, 3.17 g (yield: 92.1%), were obtained according to the same procedure as in Referential Example 2 except that 1.85 g (10 mmole) of 4-bromobenzaldehyde (purchased from Tokyo Kasei) were used instead of 3-chlorobenzaldehyde.

The α-cyano-4'-bromo-3,4-dihydroxystilbene, 544 mg (yield: 86.0%), represented by the following formula were obtained according to the same procedure as in Referential Example 3 except that 688 mg (2.00 mmole) of the above α-cyano-4'-bromo-3,4-dimethoxystilbene were used instead of α-cyano-3'-chloro-3,4-dimethoxystilbene:

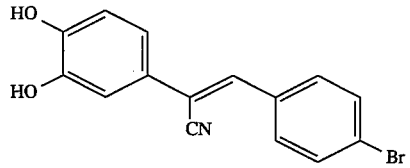

Formula 43b

The white crystalline compound, 163 mg (yield: 81.3%), represented by the following formula were obtained according to the same procedure as in Example 30 except that 158 mg (0.50 mmole) of the above α-cyano-4'-bromo-3,4-dihydroxystilbene were used instead of α-cyano-4-chloro-3',4'-dihydroxystilbene:

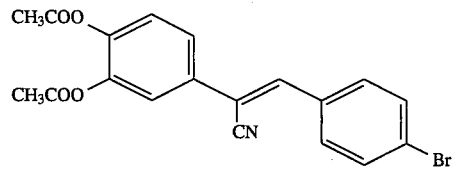

Formula 44b

The melting point of the obtained compound was 124.5° to 125.0° C.

EXAMPLE 38

The α-cyano-4-iodo-3',4'-dihydroxystilbene, 1.39 g (yield: 76.4%), represented by the following formula were obtained according to the same procedure as in Referential Example 1 except that 1.22 g (5.00 mmole) of 4-iodophenylacetonitrile obtained according to the same procedure as in Referential Example 4 were used instead of 4-chlorophenylacetonitrile:

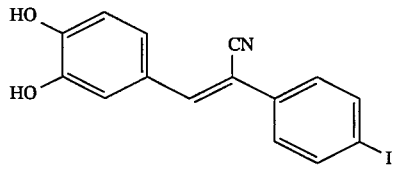

Formula 45b

The white crystalline compound, 187 mg (yield: 83.7%), represented by the following formula were obtained according to the same procedure as in Example 30 except that 182 mg (0.50 mmole) of the above α-cyano-4-iodo-3',4'-dihydroxystilbene were used instead of α-cyano-4-chloro-3',4'-dihyaroxystilbene:

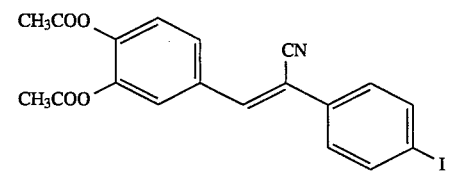

Formula 46b

The melting point of the obtained compound was 156.0° to 156.5° C.

EXAMPLE 39

The α-cyano-4'-methyl-3,4-dimethoxystilbene, 2.20 g (yield:=78.8%), were obtained according to the same procedure as in Referential Example 2 except that 1.20 g (10 mmole) of 4-methylbenzaldehyde (purchased from Wako Junyaku Kogyo) were used instead of 4-chlorobenzaldehyde.

The α-cyano-4'-methyl-3,4-dihydroxystilbene, 438 mg (yield: 87.1%), represented by the following formula were obtained according to the same procedure as in Referential Example 3 except that 559 mg (2.00 mmole) of the above α-cyano-4'-methyl-3,4-dimethoxystilbene were used instead of α-cyano-3'-chloro-3,4-dimethoxystilbene:

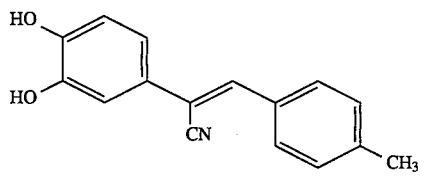

Formula 47b

The white crystalline compound, 144 mg (yield: 85.7%), represented by the following formula were obtained according to the same procedure as in Example 30 except that 126 mg (0.50 mmole) of the above α-cyano-4'-methyl-3,4-dihydroxystilbene were used instead of α-cyano-4-chloro-3',4'-dihydroxystilbene:

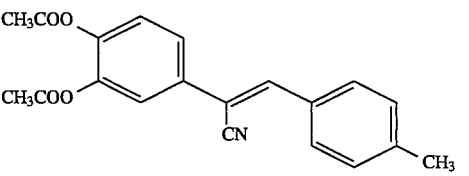

Formula 48b

The melting point of the obtained compound was 130.5° to 131.0° C.

EXAMPLE 40

The α-cyano-3'-methyl-3,4-dimethoxystilbene, 1.13 g (yield: 40.5%), were obtained according to the same procedure as in Referential Example 2 except that 1.20 g (10. 0 mmole) of 3-methylbenzaldehyde (purchased from Wako Junyaku Kogyo) were used instead of 4-chlorobenzaldehyde.

The α-cyano-3'-methyl-3,4-dihydroxystilbene, 294 mg (yield: 58.5%), represented by the following formula were obtained according to the same procedure as in Referential Example 3 except that 559 mg (2.00 mmole) of the above α-cyano-3'-methyl-3,4-dimethoxystilbene were used instead of α-cyano-3'-chloro-3,4-dimethoxystilbene:

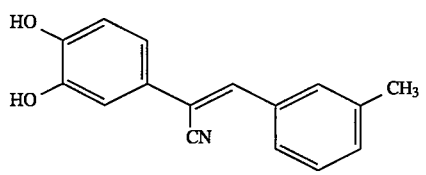

Formula 49b

The white crystalline compound, 102 mg (yield: 61.0%), represented by the following formula were obtained according to the same procedure as in Example 30 except that 126 mg (0.50 mmole) of the above α-cyano-3'-methyl-3,4-dihydroxystilbene were used instead of α-cyano-4-chloro-3',4'-dihydroxystilbene:

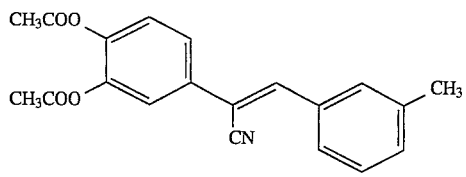

Formula 50b

The melting point of the obtained compound was 87.5° to 88.0° C.

EXAMPLE 41

The α-cyano-4'-ethyl-3,4-dimethoxystilbene, 1.79 g (yield: 61.0%), were obtained according to the same procedure as in Referential Example 2 except that 1.34 g (10.0 mmole) of 4-ethylbenzaldehyde (purchased from Tokyo Kasei) were used instead of 3-chlorobenzaldehyde.

The α-cyano-4'-ethyl-3,4-dihydroxystilbene, 448 mg (yield: 84.4%), represented by the following formula were obtained according to the same procedure as in Referential Example 3 except that 587 mg (2.00 mmole) of the above α-cyano-4'-ethyl-3,4-dimethoxystilbene were used instead of α-cyano-3'-chloro-3,4-dimethoxystilbene:

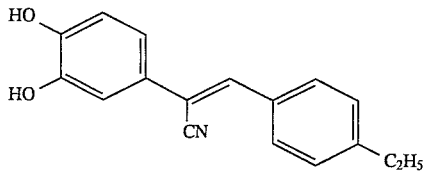

Formula 51b

The white crystalline compound, 131 mg (yield: 74.8%), represented by the following formula were obtained according to the same procedure as in Example 30 except that 133 mg (0.50 mmole) of the above α-cyano-4'-ethyl-3,4-dihydroxystilbene were used instead of α-cyano-4-chloro-3',4'-dihydroxystilbene:

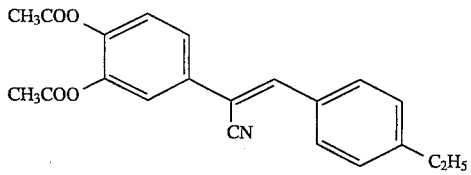

Formula 52b

The melting point of the obtained compound was 90.5° to 91.0° C.

EXAMPLE 42

The α-cyano-4-trifluoromethyl-3',4'-dihydroxystilbene, 657 mg (yield: 87.4%), represented by the following formula were obtained according to the same procedure as in Referential Example 1 except that 926 mg (5.00 mmole) of trifluoromethylphenylacetonitrile (purchased from Aldrich) were used instead of 4-chlorophenylacetonitrile:

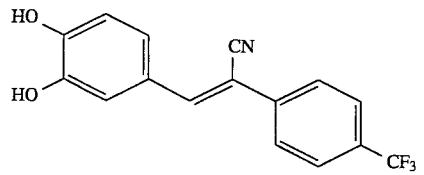

Formula 53b

The white crystalline compound, 120 mg (yield: 61.6%), represented by the following formula were obtained according to the same procedure as in Example 30 except that 153 mg (0.50 mmole) of the above α-cyano-4-trifluoromethyl-3',4'-dihydroxystilbene were used instead of α-cyano-4-chloro-3',4'-dihydroxystilbene:

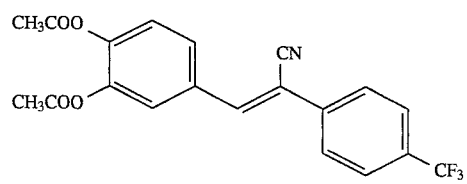

Formula 54b

The melting point of the obtained compound was 138.5° to 139.0° C.

EXAMPLE 43

The α-cyano-4-methoxy-3',4'-dihydroxystilbene, 214 mg (yield: 16.0%), represented by the following formula were obtained according to the same procedure as in Referential Example 1 except that 736 mg (5.00 mmole) of 4-methoxyphenylacetonitrile (purchased from Aldrich) were used instead of 4-chlorophenylacetonitrile:

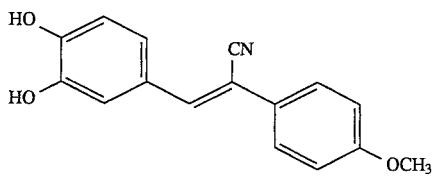

Formula 55b

The light yellow crystalline compound, 87 mg (yield: 50%), represented by the following formula were obtained according to the same procedure as in Example 30 except that 134 mg (0.50 mmole) of the above α-cyano-4-methoxy-3',4'-dihydroxystilbene were used instead of α-cyano-4-chloro-3',4'-dihydroxystilbene:

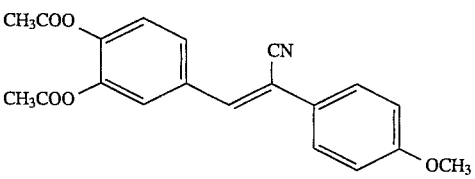

Formula 56b

The melting point of the obtained compound was 131.0° to 131.5° C.

EXAMPLE 44

The α-cyano-3,4-dimethoxystilbene, 2.62 g (yield: 98.9%), were obtained according to the same procedure as in Referential Example 2 except that 1.06 g (10.0 mmole) of benzaldehyde (purchased from Wako Junyaku Kogyo) were used instead of 4-chlorobenzaldehyde.

The α-cyano-3,4-dihydroxystilbene, 253 mg (yield: 53.4%), represented by the following formula were obtained according to the same procedure as in Referential Example 3 except that 531 mg (2.00 mmole) of the above α-cyano-3,4-dimethoxystilbene were used instead of α-cyano-3'-chloro-3,4-dimethoxystilbene:

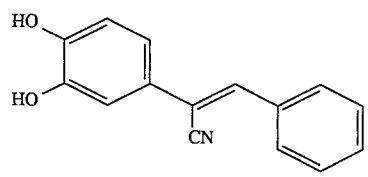

Formula 57b

The white crystalline compound, 113 mg (yield: 70.2%), represented by the following formula were obtained according to the same procedure as in Example 30 except that 119 mg (0.50 mmole) of the above α-cyano-3,4-dihydroxystilbene were used instead of α-cyano-4-chloro-3',4'-dihydroxystilbene:

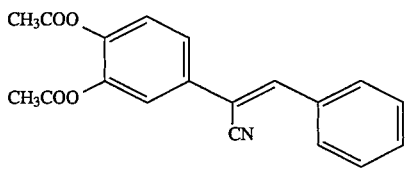
Formula 58b

The melting point of the obtained compound was 148.5° to 149.0° C.

EXAMPLE 45

The α-cyano-4-nitro-3',4'-dihydroxystilbene ¼ hydride, 1.18 g (yield: 82.3%), represented by the following formula were obtained according to the same procedure as in Referential Example 1 except that 811 mg (5.00 mmole) of 4-nitrophenylacetonitrile (purchased from Aldrich) were used instead of 4-chlorophenylacetonitrile, that the reaction product was stirred at room temperature for 4 hours and that purification was performed according to recrystallization from ethanol-water:

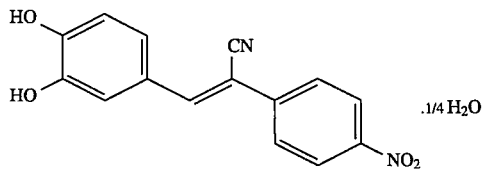
Formula 59b

The yellow crystalline compound, 110 mg (yield: 60.2%), represented by the following formula were obtained according to the same procedure as in Example 31 except that 144 mg (0.50 mmole) of the above α-cyano-4-nitro-3',4'-dihydroxystilbene ¼ hydride were used instead of α-cyano-4-chloro-3',4'-dihydroxystilbene, that 0.11 ml of acetyl chloride (purchased from wako Junyaku Kogyo) were used instead of propionyl chloride and that 0.21 ml of triethylamine (purchased from Kokusan Kagaku) were used:

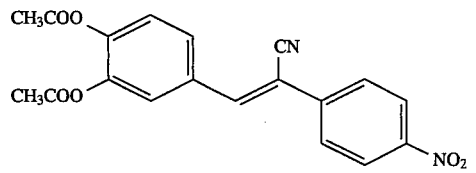
Formula 60b

The melting point of the obtained compound was 173.5° to 174.0° C.

EXAMPLE 46

The α-(thiophen-2-ylmethylidene)-3,4-dimethoxybenzeneacetonitrile, 2.49 g (yield: 91.9%), were obtained according to the same procedure as in Referential Example 2 except that 1.12 g (10.0 mmole) of thiophene-2-carboxaldehyde (purchased from Tokyo Kasei) were used instead of 3-chlorobenzaldehyde.

The α-(thiophen-2-ylmethylidene)-3,4-dihydroxybenzeneacetonitrile, 344 mg (yield: 70.7%), represented by the following formula were obtained according to the same procedure as in Referential Example 3 except that 543 mg (2.00 mmole) of the above α-(thiophen-2-ylmethylidene)-3,4-dimethoxybenzeneacetonitrile were used instead of α-cyano-3'-chloro-3,4-dimethoxystilbene:

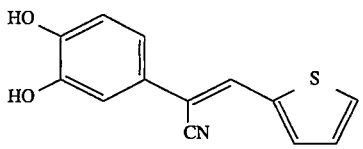
Formula 61b

The light brown crystalline compound, 122 mg (yield: 74.4%), represented by the following formula were obtained according to the same procedure as in Example 30 except that 122 mg (0.50 mmole) of the above α-(thiophen-2-ylmethylidene)-3,4-dihydroxybenzeneacetonitrile were used instead of α-cyano-4-chloro-3',4'-dihyaroxystilbene:

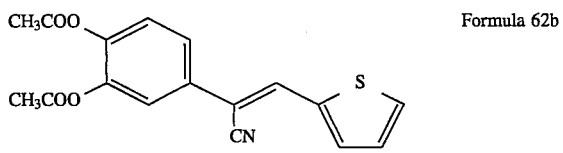
Formula 62b

The melting point of the obtained compound was 162.0° to 162.5° C.

EXAMPLE 47

The α-(thiophen-3-ylmethylidene)-3,4-dimethoxybenzeneacetonitrile, 2.12 g (yield: 78.2%), were obtained according to the same procedure as in Referential Example 2 except that 1.12 g (10.0 mmole) thiophene-3-carboxaldehyde (purchased from Tokyo Kasei) were used instead of 3-chlorobenzaldehyde.

The α-(thiophen-2-ylmethylidene)-3,4-dihydroxybenzeneacetonitrile, 344 mg (yield: 70.7%), represented by the following formula were obtained according to the same procedure as in Referential Example 3 except that 543 mg (2.00 mmole) of the above α-(thiophen-3-ylmethylidene)-3,4-dimethoxybenzeneacetonitrile were used instead of α-cyano-3'-chloro-3,4-dimethoxystilbene:

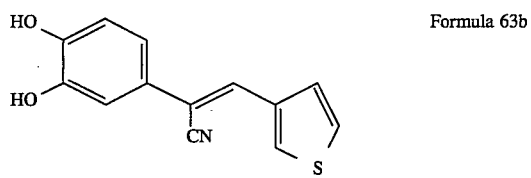
Formula 63b

The light brown crystalline compound, 121 mg (yield: 74.2%), represented by the following formula were obtained according to the same procedure as in Example 30 except that 122 mg (0.50 mmole) of the above α-(thiophen-3-ylmethylidene)-3,4-dihydroxybenzeneacetonitrile were used instead of α-cyano-4-chloro-3',4'-dihydroxystilbene:

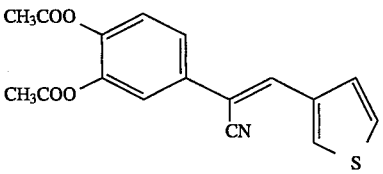
Formula 64b

The melting point of the obtained compound was 143.5° to 144.0° C.

EXAMPLE 48

The α-(3,4-dihydroxybenzylidene)-4-bromothiophene-2-acetonitrile, 1.05 g (yield: 65.0%), represented by the following formula were obtained according to the same procedure as in Referential Example 1 except that 1.01 g (5.00 mmole) of 4-bromothiophen-2-ylacetonitrile obtained according to the same procedure as in Referential Example 5 were used instead of 4-chlorophenylacetonitrile:

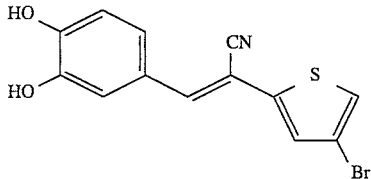

Formula 65b

The light yellow compound, 150 mg (yield: 73.8%), represented by the following formula were obtained according to the same procedure as in Example 31 except that 161 mg (0.50 mmole) of the above α-(3,4-dihydroxybenzylidene)-4-bromothiophene-2-acetonitrile were used instead of α-cyano-4-chloro-3',4'-dihydroxystilbene, that 0.11 ml of acetyl chloride (purchased from Wako Junyaku Kogyo) were used instead of propionyl chloride and that 0.21 ml of triethylamine (purchased from Kokusan Kagaku) were used:

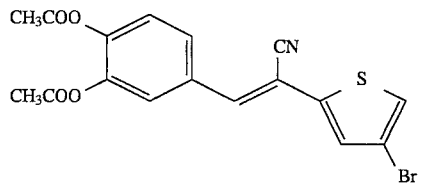

Formula 66b

The melting point of the obtained compound was 125.5° to 126.0° C.

EXAMPLE 49

The α-(5-methylthiophen-2-ylmethylidene)-3,4-dimethoxybenzeneacetonitrile, 2.36 g (yield: 82.8%), were obtained according to the same procedure as in Referential Example 2 except that 1.26 9 (10.0 mmole) of 5-methylthiophene-2-carboxaldehyde (purchased from Tokyo Kasei) were used instead of 3-chlorobenzaldehyde:

The α-(5-methylthiophen-2-ylmethylidene)-3,4-dihydroxybenzeneacetonitrile, 400 mg. (yield: 77.8%), represented by the following formula were obtained according to the same procedure as in Referential Example 3 except that 571 mg (2.00 mmole) of the above α-(5-methylthiophen-2-ylmethylidene)-3,4-dimethoxybenzeneacetonitrile were used instead of α-cyano-3'-chloro-3,4-dimethozystilbene:

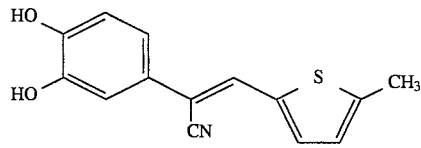

Formula 67b

The orange compound, 141 mg (yield: 82.8%), represented by the following formula were obtained according to the same procedure as in Example 30 except that 129 mg (0.50 mmole) of the above α-(5-methylthiophen-2-ylmethylidene)-3,4-dihydroxybenzeneacetonitrile were used instead of α-cyano-4-chloro-3',4'-dihydroxystilbene:

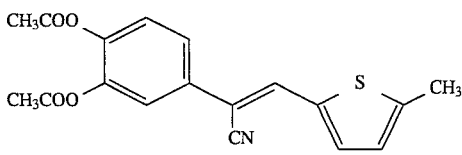

Formula 68b

The melting point of the obtained compound was 161.0° to 161.5° C.

EXAMPLE 50

The α-(5-methylfuran-2-ylmethylidene)-3,4-dimethoxybenzeneacetonitrile, 2.16 g (yield: 80.3%), were obtained according to the same procedure as in Referential Example 2 except that 1.10 g (10.0 mmole) of 5-methylfuran-2-carboxaldehyde (purchased from Wako Junyaku Kogyo) were used instead of 3-chlorobenzaldehyde.

The α-(5-methylfuran-2-ylmethylidene)-3,4-dihydroxybenzeneacetonitrile, 320 mg (yield: 66.3%), represented by the following formula were obtained according to the same procedure as in Referential Example 3 except that 539 mg (2.00 mmole) of the above α-(5-methylfuran-2-ylmethylidene)-3,4-dimethoxybenzeneacetonitrile were used instead of α-cyano-3'-chloro-3,4-dimethoxystilbene:

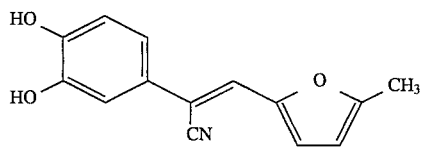

Formula 69b

The yellow compound, 31 mg (yield: 19%), represented by the following formula were obtained according to the same procedure as in Example 30 except that 121 mg (0.50 mmole) of the above α-(5-methylfuran-2-ylmethylidene)-3,4-dihydroxybenzeneacetonitrile were used instead of α-cyano-4-chloro-3',4'-dihydroxystilbene:

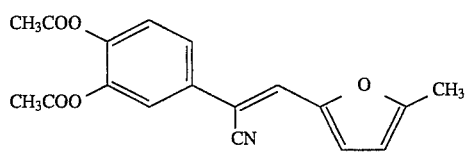

Formula 70b

The melting point of the obtained compound was 199.5° to 200.0° C.

EXAMPLE 51

The α-cyano-4-chloro-3',4',5'-trihydroxystilbene, 344 mg (yield: 23.9%), represented by the following formula were obtained according to the same procedure as in Referential Example 1 except that 771 mg (5.00 mmole) of 3,4,5-trihydroxybenzaldehyde (purchased from Aldrich) were used instead of 3,4-dihydroxybenzaldehyde:

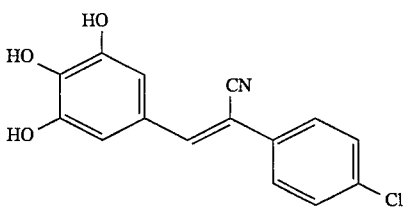

Formula 71b

The white compound, 191 mg (yield: 92.4%), represented by the following formula were obtained according to the same procedure as in Example 31 except that 144 mg (0.50 mmole) of the above α-cyano-4-chloro-3',4',5'-trihydroxystilbene were used instead of α-cyano-4-chloro-3',4'-dihydroxystilbene, that 0.14 ml of acetyl chloride (purchased from Wako Junyaku Kogyo) were used instead of propionyl chloride and that 0.28 ml of triethylamine (purchased from Kokusan Kagaku) were used:

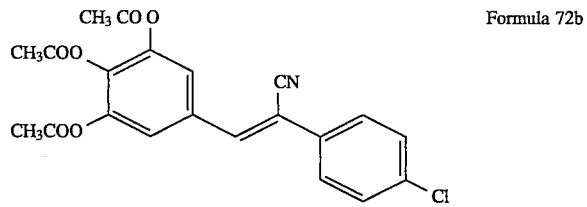

Formula 72b

The melting point of the obtained compound was 203.0° to 203.5° C.

EXAMPLE 52

A mixture with the following composition per tablet was prepared and tableted by means of a tabletor according to an ordinary manner to produce a medicine inhibiting 12-lipoxgenase selectively according to the present invention.

| | |
|---|---|
| Compound obtained in Example 34 | 20.0 (mg) |
| Lactose (purchased from Iwaki Seiyaku | 40.0 |
| Cornstarch (purchased from Yoshida Seiyaku | 15.0 |
| Magnesium stearate (purchased from Taihei Kagaku) | 0.4 |
| carboxymethyl cellulose calcium (purchased from Nichirin Kagaku Kogyo) | 20.0 |

EXAMPLE 53

A mixture with the following composition per capsule was prepared and put into a gelatin capsule according to an ordinary manner to produce a medicine inhibiting 12-lipoxgenase selectively according to the present invention.

| | |
|---|---|
| Compound obtained in Example 34 | 20.0 (mg) |
| Lactose (purchased from Iwaki Seiyaku | 40.0 |
| Finely powdered cellulose (purchased from Nippon Soda) | 30.0 |
| Magnesium stearate (purchased from Taihei Kagaku) | 3.0 |

The measured values of the nuclear magnetic resonance spectra and infrared absorption spectra of the compounds prepared in the following Examples are shown in Table 24. The nuclear magnetic resonance spectra [$^1$H-NMR (500 MHz)] were measured in a DMSO-$d_6$ solvent with tetramethylsilane as internal standard, and the infrared absorption spectra were measured according to a KBr tablet method.

TABLE 24

| Compound | Structural formula | $^1$H-NMR (DMSO.$d_6$, δppm) | IR (vcm$^{-1}$) |
|---|---|---|---|
| Formula 22c | | 6.88(1H, d), 7.29(1H, d), 7.47(1H, I), 7.52(1H, I), 7.55(1H, s), 7.60 (1H, s), 8.02(1H, s), 8.06(1H, d), 8.09(1H, d) | 3520, 3325, 2225, 1620, 1590, 1530, 1455, 1430, 1370, 1300, 1290, 1270, 1240, 1200, 1165, 1120, 1110, 755, 735 |
| Formula 23c | | 6.89(1H, d) 7.35(1H, dd), 7.57(2H, m), 7.60(1H, d), 7.92(1H, dd), 7.94(1H, dd), 7.96(1H, s), 8.02 (2H, d), 8.19(1H, d) | 3440, 3350, 3060, 2230, 1610, 1580, 1520, 1460, 1350, 1315, 1305, 1290, 1230, 1195, 1130, 1115, 860, 820, 810, 755, 740 |
| Formula 24c | | 6.87(1H, d), 7.13(1H, dd), 7.21(1H, d), 7.60(2H, m), 7.92(1H, s), 7.97 (2H, m), 8.03(1H, d), 8.06(1H, dd), 8.37(1H, d) | 3300, 3070, 2225, 1605, 1535, 1450, 1440, 1380, 1300, 1280, 1230, 1130, 1110, 860, 810, 740 |
| Formula 25c | | 6.88(1H, d), 7.21(1H, dd), 7.28 (1H, d), 7.63(3H, m), 7.93(1H, d), 8.03(2H, m), 8.12(1H, m), 8.41 (1H, s) | 3560, 3450, 3375, 3060, 2220, 1605, 1525, 1440, 1350, 1295, 1215, 1205, 1180, 1120, 800, 775, 760 |

TABLE 24-continued

| Compound | Structural formula | ¹H-NMR (DMSO.d₆, δppm) | IR (vcm⁻¹) |
|---|---|---|---|
| Formula 26c | (structure shown) | 6.86(1H, d), 7.13(1H, dd), 7.19 (1H, d), 7.32(1H, t), 7.43(1H, I), 7.45(1H, s), 7.62(1H, d), 7.74(1H, s), 7.76(1H, d) | 3400, 3075, 2230, 1620, 1530, 1460, 1445, 1360, 1305, 1275, 1210, 1190, 1135, 960, 865, 820, 795, 655, 640 |

Referential Example 6

[Preparation of α-(3,4-dimethoxyphenyl-β-(naphthalen-2-yl)acrylonitrile]

A mixture of 3,4-dimethyoxyphenylacetonitrile (1.77 g, 10.0 mmol, purchased from Tokyo Kasei,) and 2-naphthoaldehyde (1.56 g, 10.0 mmol, purchased from Tokyo Kasei) in 30 ml of ethanol was heated to dissolve. Two drops of 20% aqueous sodium hydroxide solution was then added and the reaction mixture was stirred over night. The precipitate was collected and washed with ethanol then with hexane, and dried to give 2.60 g (yield: 82.5%) of α-(3,4-dimethoxyphenyl-β-(naphthalen-2-yl)acrylonitrile as a yellow crystalline.

EXAMPLE 54

To a mixture of thianaphthene-3-acetonitrile (866 mg, 5.0 mmol, purchased from Lancaster) and 3,4-dihydroxybenzaldehyde (691 mg, 5.0 mmol, purchased from Tokyo Kasei) in 10 ml of ethanol was added 0.54 ml of piperidine (purchased from Wako Junyaku Kogyo) and refluxed for 8 hours. After being cooled, the mixture was poured into 100 ml of 1N-hydrochloric acid and stirred. The precipitate was collected and washed with water, then dissolved in ethyl acetate. The solution was washed with 20% aqueous sodium bisulfite solution twice and then with brine. The organic layer was dried over anhydrous sodium sulfate. The solvent was removed under reduced pressure. The residue was purified by column chromatography on silica gel. Elution with hexane-ethyl acetate (10:1–10:6) gave 580 mg (yield: 39.5%) of the product represented by the following formula as a yellow cristalline.

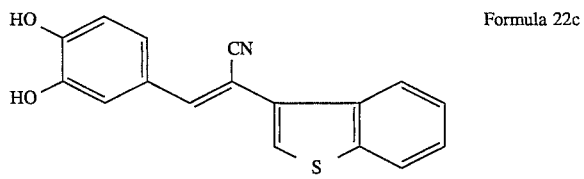

Formula 22c

EXAMPLE 55

The yellow crystalline compound, 499 mg (yield: 34.7%), represented by the following formula 23c were obtained according to the same procedure as in Example 54 except that 836 mg (5.00 mmole) of naphthalene-2-acetonitrile (purchased from Aldrich) were used instead of thianaphthene-3-acetonitrile:

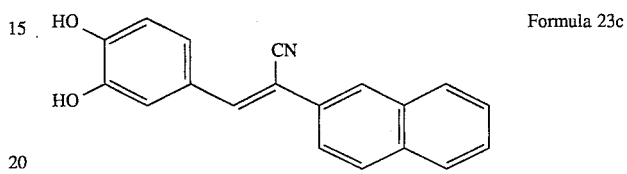

Formula 23c

The melting point of the obtained compound was 206° to 207° C.

EXAMPLE 56

A mixture of α-(3,4-dimethoxyphenyl-β-(naphthalen-2-yl)acrylonitrile (631 mg, 2.0 mmol) obtained according to the same procedure as in Referential Example 6 and pyridinium chloride (3.5 g, 30 mmol, purchased from Wako Junyaku Kogyo) was melted to mix on an oil bath(210° C.) under atmosphere of argon gas. Stirring was continued for additional one hour. After being cooled, 20 ml of 2N-hydrochloric acid was added to the resultant reaction mass and the mixture was stirred for 30 minutes. The precipitate was collected and washed with water three times, and then subjected to short column chromatography on silica gel. Elution with ethyl acetate give 490 mg (yield: 85.3%) of the product represented by the following formula:

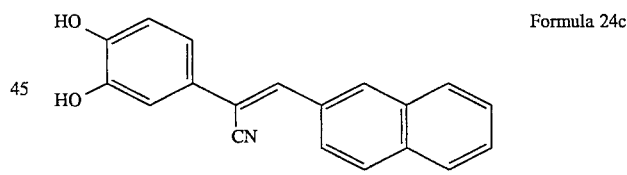

Formula 24c as a yellow crystalline, mp 166.0°–166.5° C.

EXAMPLE 57

The yellow crystals of α-(3,4-dimethoxyphenyl)-β-(naphthalen-1-yl)acrylonitrile, 2.42 g (yield: 76.8%), were obtained according to the same procedure as in Referential Examples except that 1.56 g (10.0 mmole) of 1-naphthoaldehyde (purchased from Aldrich) were used instead of 2-naphthoaldehyde.

The yellow crystalline compound, 524 mg (yield: 91.1%), represented by the following formula 25c were obtained according to the same procedure as in Example 56 except that 631 mg (2.00 mmole) of the above α-(3,4-dimethoxyphenyl)-β-(naphthalen-1-yl)acrylonitrile were used instead of α-(3,4-dimethoxyphenyl)-β-(naphthalen-2-yl)acrylonitrile:

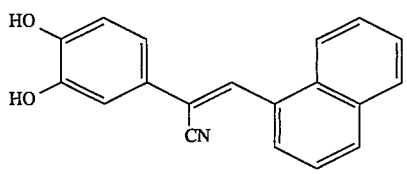
Formula 25c

The melting point of the obtained compound was 162° to 163° C.

EXAMPLE 58

The yellow crystals of α-(3,4-dimethoxyphenyl)-β-(benzofuran-2-yl)acrylonitrile, 2.46 g (yield: 80.7%), were obtained according to the same procedure as in Referential Examples except that 1.46 g (10.0 mmole) of benzofuran-2-carboxaldehyde (purchased from Lancaster) were used instead of 2-naphthoaldehyde.

The yellow crystalline compound, 457 mg (yield: 82.4%), represented by the following formula 26c were obtained according to the same procedure as in Example 56 except that 611 mg (2.00 mmole) of the above α-(3,4-dimethoxyphenyl)-β-(benzofuran-2-yl)acrylonitrile were used instead of α-(3,4-dimethoxyphenyl)-β-(naphthaien-2-yl)acrylonitrile:

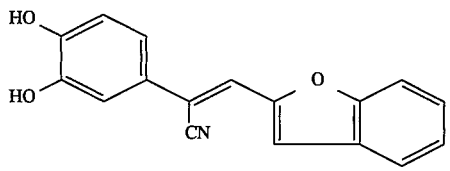
Formula 26c

The melting point of the obtained compound was 192° to 193° C.

EXAMPLE 59

A mixture with the following composition per tablet was prepared and tableted by means of a tabletor according to an ordinary manner to produce a medicine inhibiting 12-lipoxgenase selectively according to the present invention.

| | |
|---|---|
| Compound obtained in Example 58 | 20.0 (mg) |
| Lactose (purchased from Iwaki Seiyaku | 40.0 |
| Cornstarch (purchased from Yoshida Seiyaku | 15.0 |
| Magnesium stearate (purchased from Taihei Kagaku) | 0.4 |
| carboxymethyl cellulose calcium (purchased from Nichirin Kagaku Kogyo) | 20.0 |

EXAMPLE 60

A mixture with the following composition per capsule was prepared and put into a gelatin capsule according to an ordinary manner to produce a medicine inhibiting 12-lipoxgenase selectively according to the present invention.

| | |
|---|---|
| Compound obtained in Example 58 | 20.0 (mg) |
| Lactose (purchased from Iwaki Seiyaku | 40.0 |
| Finely powdered cellulose (purchased from Nippon Soda) | 30.0 |
| Magnesium stearate (purchased from Taihei Kagaku | 3.0 |

Possibilities of Industrial Utilization

As described in detail above, the present invention relates to a stilbene derivative and a stilbene homologue derivative inhibiting 12-lipoxgenase selectively, and medicines containing the above compounds as effective components and inhibiting 12-lipoxygenaee selectively; moreover, the present invention relates to novel compounds of a stilbene derivative and a stilbene homologue derivative capable of forming a substance whose modified part is cleaved in vivo and which inhibits 12-lipoxgenase selectively, and medicines containing the above compounds as effective components and capable of inhibiting 12-lipoxygenase selectively; and possibilities of the industrial utilization of the present invention are as follows:

1) The compounds of the present invention have an effect of inhibiting 12-lipoxgenase with a strong and high selectivity.
2) The medicines containing the above compounds of the present invention as effective components are useful for the prevention and remedies of various circulatory diseases such as arteriosclerosis and vasospasm and the prevention of the metastasis of some cancers.
3) The compounds of the present invention are effective as effective components of medicine inhibiting 12-lipozygenase selectively with a low toxicity and few side effects.
4) The compounds of the present invention have an effect of inhibiting 12-lipoxgenase with a strong and high selectively as their modified parts are cleaved in vivo due to the effect of enzymes.
5) lit is possible to control the cleavage in vivo of the compounds of the present invention by selecting the kinds of the acyl group as modified parts of the compounds of the present invention.

What is claimed is:

1. A compound of the formula:

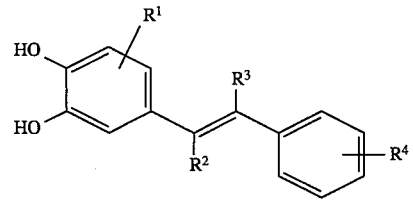

wherein $R^1$ is hydrogen or hydroxy;

$R^2$ and $R^3$ are different and each is hydrogen or cyano; and $R^4$ is lower alkyl, lower alkoxy, halogen or triflouoromethyl.

2. A composition comprising a pharmaceutically acceptable carrier and the compound of claim 1.

3. A method for inhibiting 12-lipoxgenase comprising contacting 12-lipoxgenase with of a compound of the formula:

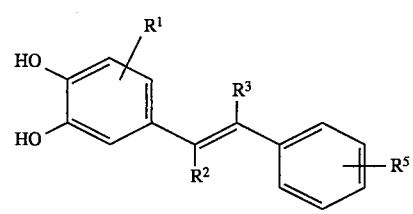

wherein $R^1$ is selected from the group consisting of hydrogen and hydroxy;

$R^2$ and $R^3$ are different and each is hydrogen or cyano; and $R^5$ is lower alkyl, lower alkoxy, halogen, trifluoromethyl or nitro.

4. The method of claim 3, wherein said contacting comprises administering an effective amount of said compound to an animal in need thereof.

5. The method of claim 4, wherein said animal is human.

6. A compound of the formula:

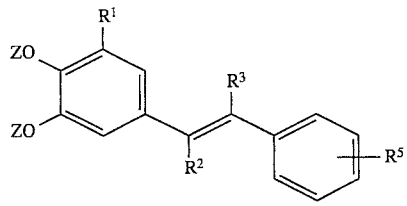

wherein $R^1$ is hydrogen or OZ;

$R^2$ and $R^3$ are different and each is hydrogen or cyano;

$R^5$ is lower alkyl, lower alkoxy, halogen, trifluoromethyl or nitro;

$R^6$ is a straight-chain $C_{1-20}$ alkyl group, a branched-chain $C_{1-20}$ alkyl group, straight-chain $C_{1-20}$ alkenyl group, or branched-chain $C_{1-20}$ alkenyl group; and Z is independently hydrogen or a group represented by the following formula 3:

wherein none of Z are hydrogen atoms at the same time.

7. A composition comprising a pharmaceutically acceptable carrier and the compound of claim 6.

8. A method for inhibiting 12-lipoxgenase comprising contacting 12-lipoxgenase with the compound according to claim 6.

9. The method of claim 8, wherein said contacting comprises administering an effective amount of said compound to an animal in need thereof.

10. The method of claim 9, wherein said animal is human.

11. A compound of the formula:

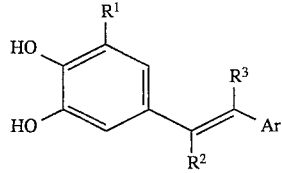

wherein $R^1$ is hydrogen or hydroxy, $R^2$ and $R^3$ are different and each is hydrogen or cyano; and Ar is naphthyl.

12. A composition comprising a pharmaceutically acceptable carrier and the compound of claim 11.

13. A method for inhibiting 12-lipoxgenase comprising contacting 12-lipoxgenase with the compound according to claim 11.

14. The method of claim 13, wherein said contacting comprises administering an effective amount of said compound to an animal in need thereof.

15. The method of claim 14, wherein said animal is human.

* * * * *